(12) United States Patent
Brinton et al.

(10) Patent No.: US 8,969,329 B2
(45) Date of Patent: Mar. 3, 2015

(54) ALLOPREGNANOLONE IN A METHOD FOR ENHANCING NEUROLOGICAL FUNCTION

(75) Inventors: Roberta Diaz Brinton, Rancho Palos Verdes, CA (US); Jun Ming Wang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 148 days.

(21) Appl. No.: 12/526,604

(22) PCT Filed: Jun. 11, 2008

(86) PCT No.: PCT/US2008/066558
§ 371 (c)(1),
(2), (4) Date: Aug. 10, 2009

(87) PCT Pub. No.: WO2008/154579
PCT Pub. Date: Dec. 18, 2008

(65) Prior Publication Data
US 2010/0105646 A1    Apr. 29, 2010

Related U.S. Application Data

(60) Provisional application No. 60/943,187, filed on Jun. 11, 2007.

(51) Int. Cl.
*A61K 31/56* (2006.01)
(52) U.S. Cl.
USPC ............................................. 514/182
(58) Field of Classification Search
USPC ............................................. 514/182
See application file for complete search history.

(56) References Cited

U.S. PATENT DOCUMENTS

| | | | |
|---|---|---|---|
| 4,897,388 | A | 1/1990 | Malluche |
| 5,925,630 | A | 7/1999 | Upasani et al. |
| 5,939,407 | A | 8/1999 | Landfield |
| 6,143,736 | A | 11/2000 | Upasani et al. |
| 6,277,838 | B1 | 8/2001 | Upasani et al. |
| 6,552,010 | B1 | 4/2003 | Schwartz et al. |
| 2004/0202651 | A1 | 10/2004 | Cohen |
| 2005/0020552 | A1 | 1/2005 | Aschkenasy |

FOREIGN PATENT DOCUMENTS

| | | |
|---|---|---|
| WO | WO 99/45931 | 9/1999 |
| WO | WO2005009359 * | 2/2005 |
| WO | WO 2005009359 A2 * | 2/2005 |
| WO | WO 2006/037016 | 4/2006 |
| WO | WO 2007/025064 | 3/2007 |

OTHER PUBLICATIONS

He et al.; "Allopregnanolone, a progressive metabolite, enhances behavioral recovery and decreases neuronal low after traumatic brain injury"; 2004; Restorative Neurology and Neuroscience; 22:19-31.*

Wikipedia; steroid hormones; http://en.wikipedia.org/wiki/Steroid_hormone, accessed Jan. 13, 2014.*
Merriam-Webster; daily definition; http://www.merriam-webster.com/dictionary/daily; accessed Jan. 13, 2014.*
Borchelt, at al., "Familial Alzheimer's disease-linked presenilin 1 variants elevate Abeta1-42/1-40 ratio in vitro and in vivo", *Neuron*, 17(5):1005-13 (1996).
Brinton, "Cellular and molecular mechanisms of estrogen regulation of memory function and neuroprotection against Alzheimer's disease: recent insights and remaining challenges", *Learn. Mem.*, 8(3):121-33 (2001).
Eriksson, et al., "Neurogenesis in the adult human hippocampus", *Nat. Med.*, 4(11):1313-7 (1998).
Erlandsson, et al., "Immature neurons from CNS stem cells proliferate in response to platelet-derived growth factor", *J. Neurosci.*, 21(10):3463-91 (2001).
Haughey, et al., "Disruption of neurogenesis by amyloid beta-peptide, and perturbed neural progenitor cell homeostasis, in models of Alzheimer's disease", *J. Neurochem.*, 83(6):1509-24 (2002).
Hawkinson, et al., "Substituted 3beta-phenylethynyl derivatives of 3alpha-hydroxy-5alpha-pregnan-20-one: remarkably potent neuroactive steroid modulators of gamma-aminobutyric acidA receptors", *J. Pharmacol. Exp. Ther.*, 287(1):198-207 (1998).
Lesne, et al., "A specific amyloid-beta protein assembly in the brain impairs memory" *Nature*, 440:352-357 (2006).
Logg, et al., "A uniquely stable replication-competent retrovirus vector achieves efficient gene delivery in vitro and in solid tumors", *Hum. Gene Ther.*, 12(8):921-32 (2001).
Monje and Palmer, "Radiation injury and neurogenesis", *Curr. Opin. Neurol.*, 16(2):129-34 (2003).
Song, et al., "Neural stem cells from adult hippocampus develop essential properties of functional CNS neurons", *Nat. Neurosci.*, 5(5):438-45 (2002).
Van Praag, et al., "Functional neurogenesis in the adult hippocampus", *Nature*, 415(6875):1030-4 (2002).

* cited by examiner

*Primary Examiner* — Rei-tsang Shiao
(74) *Attorney, Agent, or Firm* — Pabst Patent Group LLP

(57) ABSTRACT

Neuro-enhancing agents, compositions and methods are disclosed herein. Preferred neuro-enhancing agents of the present invention include progesterone and metabolites of progesterone, such as 3α-hydroxy-5α-pregnan-20-one (THP). These agents yield neuro-enhancing effects on neural cells that include neural progenitor and/or stem cells, whereby the agents stimulate mitosis of neural progenitor cells, stimulate neurite growth and organization, protect against neural loss, or one or more of these neural processes. Thus, the neuro-enhancing agents, compositions and methods disclosed herein are useful to reverse or prevent neurological disease or defects associated with neural loss or degeneration, such as Alzheimer's disease, neurological injuries, including injuries resulting from radiation therapy, and age-related neurological decline, including impairments in memory and learning.

22 Claims, 9 Drawing Sheets a - p<0.01 @ 1 Hour
b - p<0.0009 @ 8 Hours
c - p<0.0001 @ 24 Hours
d - p<0.002 @ 1 Hours
e - p<0.0001 @ 8 and 24 Hours
f - p<0001 @ 1 Hour
g - p<0.0005 @ 8 Hours
h - p<0.0001 @ 24 Hours

ALLOPREGNANOLONE IN A METHOD FOR ENHANCING NEUROLOGICAL FUNCTION

CROSS-REFERENCE TO RELATED APPLICATIONS

This application is a filing under 35 U.S.C. 371 of PCT/US2008/066558 filed with the U.S. Receiving Office of the Patent Cooperation Treaty on Jun. 11, 2008, and claims priority to and benefit of U.S. Ser. No. 60/943,187 by Brinton et al. entitled "Agents, Compositions, and Methods for Enhancing Neurological Function" filed on Jun. 11, 2007, and where permissible are incorporated herein in their entirety.

FIELD OF THE INVENTION

This invention is in the field of pharmaceutical compositions for enhancing neurological function and methods of use thereof, particularly compositions containing allopregnanolone or a derivative or analogue thereof.

BACKGROUND OF THE INVENTION

The mammalian nervous system includes a peripheral nervous system (PNS) and a central nervous system (CNS), including the brain and spinal cord, and is composed of two principal classes of cells, namely neurons and glial cells. The glial cells fill the spaces between neurons, nourishing them and modulating their function. During development, differentiating neurons from the central and peripheral nervous systems send out axons that grow and make contact with specific target cells. In some cases, axons must cover enormous distances with some growing into the periphery, whereas others are confined within the central nervous system. In mammals, this stage of neurogenesis is thought to be complete during the embryonic phase of life. Further, neuronal cells are generally thought not to multiply once they have fully differentiated.

A host of neuropathies, including neurodegenerative diseases, have been identified that affect the nervous system of mammals. These neuropathies, which may affect neurons themselves or associated glial cells, may result from cellular metabolic dysfunction, infection, injury, exposure to toxic agents, autoimmunity, malnutrition, and/or ischemia or may be due to age-related neurological changes. In some cases, the neuropathy is thought to induce cell death directly. In other cases, the neuropathy may induce sufficient tissue necrosis to stimulate the body's immune/inflammatory system and the immune response to the initial injury then destroys neural pathways. Also, neuronal tissue may be lost as a result of physical insult or trauma.

Loss of neurons, either directly or indirectly, was thought to be irreversible in the adult human brain, as it was long held that the generation of new neurons did not occur in the mature brain. In most brain regions, the generation of neurons is generally confined to a discrete developmental period. However, notable exceptions are found in the dentate gyrus and the subventricular zone of several species, where it has been shown that new neurons are generated well into the postnatal and adult period. Granule neurons are generated throughout life from a population of continuously dividing neural progenitor cells residing in the subgranular zone of the dentate gyms in the rodent brain.

"Newborn" neurons generated from these neural progenitor cells migrate into the granule cell layer, differentiate, extend axons and express neuronal marker proteins. The mechanisms and appropriate stimuli that promote the generation of new neurons, however, are largely unknown.

Attempts to counteract the effects of acute or neurodegenerative lesions of the brain and/or spinal cord have primarily involved implantation of embryonic neurons in an effort to compensate for lost or deficient neural or neurological function. However, human fetal cell transplantation research is severely restricted. Administration of neurotrophic factors, such as nerve growth factor and insulin-like growth factor, also has been suggested to stimulate neuronal growth within the CNS.

To date, however, no satisfactory agents or treatment methods exists to repair, or counteract, the neuronal damage associated with neuropathies, such as Parkinson's disease and Alzhemier's disease, neurological injury or neurological age-related decline or impairment. Accordingly, there is a need for new treatment modalities directed to improving the adverse neurological conditions associated with neuropathies, neurological injuries and age-related neurological decline or impairment.

Therefore, it is an object of the invention to provide compositions for the treatment or prevention of neuronal damage associated with neuropathies, such as Parkinson's disease and Alzheimer's disease, neurological injury or neurological age-related decline or impairment, and methods of making and using thereof.

SUMMARY OF THE INVENTION

Compositions for the treatment or prevention of neuronal damage associated with neuropathies, such as Parkinson's disease and Alzheimer's disease, neurological injury or neurological age-related decline or impairment, and methods of making and using thereof are described herein. In one embodiment, the composition contains $\alpha$-hydroxy-5$\alpha$-pregnan-20-one (also referred to as allopregnanolone, THP, or AP$\alpha$), a derivative, analogue or prodrug thereof, or a pharmaceutically acceptable salt thereof. Suitable analogues or derivatives of THP include, but are not limited to, 3 beta-phenylethynyl derivatives of 3$\alpha$-hydroxy-5$\alpha$-pregnan-20-one, analogues or derivatives of molecules of 3$\alpha$-hydroxy-5$\alpha$-pregnan-20-one that exhibit substantially equivalent neuro-enhancing activity as 3$\alpha$-hydroxy-5$\alpha$-pregnan-20-one, progesterone, and progesterone-like molecules, which are either natural metabolites of progesterone or synthetic variants of progesterone, and exhibit substantially equivalent neuro-enhancing activity as 3$\alpha$-hydroxy-5$\alpha$-pregnan-20-one.

Effective therapeutic amounts of the neuro-enhancing agents will depend on the neurological disease or defect being targeted, but generally range from about 0.1 mg to 1000 mg, preferably from about 0.1 to 500 mg, more preferably from about 0.1 to about 100 mg. In one embodiment, the compositions contain at least about 10 mg or greater of the pharmaceutically active form of 3$\alpha$-hydroxy-5$\alpha$-pregnan-20-one or an analogue, derivative, or prodrug thereof.

The compositions can be administered on a daily basis or less frequently, for example, every other day, once a week, once a month, etc. The compositions can be administered in a single dose or multiple doses. The effective administration periods depend on the particular neurological disease or defect being targeted. Generally effective administration periods are about one month or longer, but can be about six months to about one year or longer.

The compositions can be formulated for oral, enteral, topical, or transdermal administration. The compositions can further contain one or more pharmaceutically acceptable excipients, carriers, and/or additives. In one embodiment, the compositions are formulated for oral administration. Suitable oral dosage forms include, but are not limited to, tablets, soft or hard, gelatin, or non-gelatin capsules, caplets, solutions, syrups, and suspensions.

In one embodiment, the compositions are administered to enhance neurological function in an individual with a neurological disease, neurological injury or age-related neuronal decline or impairment. The compositions are administered over a period of time effective to stimulate neural mitosis, to prevent neuronal loss, or combination thereof. Target neurological dysfunctions and disease states include Alzheimer's disease; neurological injuries, including those following radiation therapy for brain-related cancers; and age-related memory decline and age-related learning impairments. In one embodiment, the compositions are administered to reduce β-amyloid accumulation in the brain, which is associated with Alzheimer's disease. The methods for enhancing neurological function in an individual can be practiced in-vivo and/or ex-vivo. The compositions can also be administered to improve or restore neurological function by inducing or stimulating the generation of new neurons, protecting against neuronal loss, stimulating or inducing neurite outgrowth and organization or protecting against loss of neurites and neural networks, or combination thereof.

DETAILED DESCRIPTION OF THE INVENTION

I. Definitions

Figure 1:
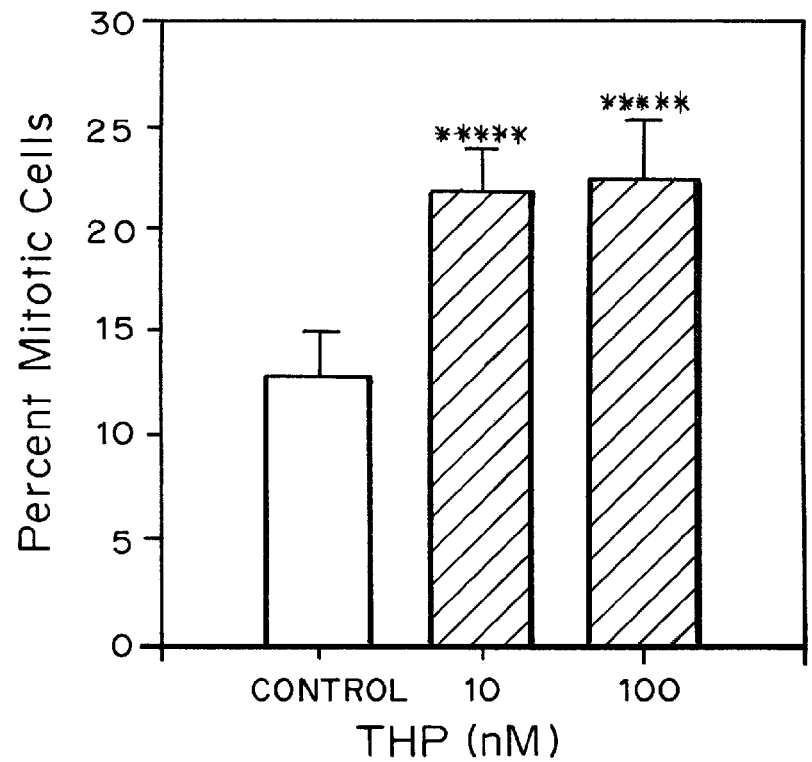
FIG. 1 depicts a graphic representation of the effect of 3α-hydroxy-5α-pregnan-20-one (THP) administration (nanomolar, nM) on the percent of the total number of hippocampal neural cells exhibiting a mitotic appearance, i.e., exhibiting a doublet form cell body indicative of mitosis.

The term "analogue", as used herein, refers to a chemical compound with a structure similar to that of another (reference compound) but differing from it in respect to a particular component, functional group, atom, etc.

The term "derivative", as used herein, refers to compounds which are formed from a parent compound by one or more chemical reaction(s).

The term "prodrug", as used herein, refers to an active drug chemically transformed into a per se inactive derivative which, by virtue of chemical or enzymatic attack, is converted to the parent drug within the body before or after reaching the site of action. Prodrugs are frequently (though not necessarily) pharmacologically inactive until converted to the parent drug.

"Pharmaceutically acceptable salt", as used herein, refer modification of the parent compound by making the acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Modified release dosage form: A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release, extended release, and pulsatile release dosage forms and their combinations are types of modified release dosage forms.

Delayed release dosage form: A delayed release dosage form is one that releases a drug (or drugs) at a time other than promptly after administration.

Extended release dosage form: An extended release dosage form is one that allows at least a twofold reduction in dosing frequency as compared to the drug presented as a conventional dosage form (e.g. as a solution or prompt drug-releasing, conventional solid dosage fond).

Pulsatile release dosage form: A pulsatile release dosage form is one that mimics a multiple dosing profile without repeated dosing and allows at least a twofold reduction in dosing frequency as compared to the drug presented as a conventional dosage form (e.g. as a solution or prompt drug-releasing, conventional solid dosage form). A pulsatile release profile is characterized by a time period of no release (lag time) or reduced release followed by rapid drug release.

II. Compositions

A. Neuro-Enhancing Agents

The compositions described herein contain one or more neuro-enhancing agents. In one embodiment, the one or more neuro-enhancing agents are selected from progesterone or an analogue or derivative thereof, such as precursors of progesterone, progesterone metabolites and progesterone derivatives in its metabolic pathway, as well as the salts or hydrates of these analogues and derivatives. In a preferred embodiment, the compositions contains a naturally occurring metabolite of progesterone, 3α-hydroxy-5α-pregnan-20-one (APα), also known as tetrahydroprogesterone (THP), as well as the pharmaceutically acceptable salts and hydrates thereof. 3α-hydroxy-5α-pregnan-20-one (THP) is generally classified a neurosteriod as it is produced in the central nervous system and previously has been found to be an allosteric modulator of GABA receptors. See, for example, U.S. Pat. Nos. 5,925,630; 6,143,736; and 6,277,838.

Other suitable analogs and derivatives include variant molecules of 3α-hydroxy-5α-pregnan-20-one or substituted derivatives of 3α-hydroxy-5α-pregnan-20-one, such as 3α-oxy derivatives, 3α-alkyl derivatives, 3α-alkenyl derivatives, 3α-ester derivatives, 3α-ether derivatives; 3ss-phenylethynyl derivatives of 3α-hydroxy-5α-pregnan-20-one, and 3p-phenylethynyl derivatives of 3α-hydroxy-5α-pregnan-20-one, as described in Hawkinson, et al. *J. Pharmacology & Experimental Therapeutics* 287: 198-207 (1998); as well as steroids derivatives of the 5α pregnan-20-one series such as those described in U.S. Pat. Nos. 5,925,630, 6,143,736 and 6,277,838.

Analogs or derivatives of 3α-hydroxy-5α-pregnan-20-one include progesterone-like molecules that are either natural precursors or metabolites of progesterone or synthetic variants of progesterone that exhibit substantially equivalent neurogenic activity as 3α-hydroxy-5α-pregnan-20-one. Substantially equivalent neuro-enhancing activity is defined as approximately 30% to approximately 300% of the neuro-enhancing activity of 3α-hydroxy-5α-pregnan-20-one.

The neuro-enhancing agents are administered at dosages and for periods of time effective to stimulate or induce neural proliferation and/or to protect against the neural loss in an individual. Dosage regimes may be adjusted for purposes of improving the therapeutic response to the particular composition administered. For example, several divided doses may be administered daily or the dose may be proportionally reduced as indicated by the exigencies of the therapeutic situation. The dosages of the one or more neuro-enhancing agents is in the range of about 0.1 mg to about 1000 mg, more preferably in the range of about 1 mg to about 500 mg, most preferably in the range from about 10 mg to about 100 mg. However, the particular dose depends on the particular neurological disease or defect being targeted and can be readily determined by the treating physician.

The compounds described herein may have one or more chiral centers and thus exist as one or more stereoisomers. Such stereoisomers can exist as a single enantiomer, a mixture of diastereomers or a racemic mixture. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

B. Additional Active Agents

The compositions can further contain one or more additional active agents. In one embodiment, the additional active agent is a steroid. Suitable steroids include biologically active forms of vitamin D3 and D2, such as those described in U.S. Pat. Nos. 4,897,388 and 5,939,407. The steroids may be co-administered to further aid in neurogenic stimulation or induction and/or prevention of neural loss, particularly for treatments of Alzheimer's disease. Estrogen and estrogen related molecules also may be co-administered with the neuro-enhancing agents to enhance neuroprotection as described in Brinton (2001) *Learning and Memory* 8 (3): 121-133.

Other neuroactive steroids, such as various forms of dehydroepiandrosterone (DHEA) as described in U.S. Pat. No. 6,552,010, can also be co-administered to further aid in neurogenic stimulation or induction and/or prevention of neural loss. Other agents that cause neural growth and outgrowth of neural networks, such as Nerve Growth Factor (NGF), Brain-derived Neurotrophic Factor (BDNF), can also be administered either along with or before or after the administration of THP. Additionally, inhibitors of neural apoptosis, such as inhibitors of calpains and capases as described in Haughey et al. (2002) *J Neurochemistry* 83: 1509-1524, and other cell death mechanisms, such as necrosis, can be co-administered with the neuro-enhancing agents to further prevent neural loss associated with certain neurological diseases and neurological defects.

C. Formulations

Depending upon the manner of introduction, the neuro-enhancing agents described herein may be formulated in a variety of ways. Formulations containing THP or other substantially equivalent variant molecules can be prepared in various pharmaceutical forms, such as granules, tablets, capsules, suppositories, powders, controlled release formulations, suspensions, emulsions, creams, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized.

1. Excipients, Carriers, and Additives.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, P A: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The proportion of pharmaceutically active neuro-enhancing agent to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

2. Modified Release Formulations

The compositions described herein can be formulation for modified or controlled release. Examples of controlled release dosage forms include extended release dosage forms, delayed release dosage forms, pulsatile release dosage forms, and combinations thereof.

Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more neuro-protective agents. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

III. Methods of Use

The compositions described herein provide an effective amount of one or more neuro-enhancing agents upon administration to an individual. As used in this context, an "effective amount" of one or more neuro-enhancing agents is an amount that is effective to improve or ameliorate one or more symptoms associated with a particular neurological disease, neurological defect or age-related neurological decline or impairment. Such a therapeutic effect is generally observed within about 4 to about 6 weeks of initiating administration of a composition containing an effective amount of one or more neuro-enhancing agents, although the therapeutic effect may be observed in less than 4 weeks or greater than 6 weeks.

The individual is preferably a mammal, and more preferably the mammal is a human who has lost some amount of neurological function as a result of neurological disease, neurological injury or age-related neurological decline or impairment. Generally neural loss implies any neural loss at the cellular level, including loss in neurites, neural organization or neural networks. Examples of other subjects who can be treated include humans, dogs, cats, rats, and mice. Lower mammal models using, for example, rats or mice can be used to predict modes of general brain aging and associated neuronal loss in higher mammals, such as humans.

The compositions are preferably, though not necessarily, administered daily, in an amount to provide about a 1%, to about 25% increase in the blood level of the one or more neuro-enhancing agents described herein. Generally, the total daily dosage will be at least about 10 mg and more preferably at least about 50 mg, and preferably not more than 500 mg per day, administered orally. Capsules or tablets for oral delivery can contain up to a full daily oral dose, e.g., 100 mg or more. Where the administration is by other than an oral route, the neuro-enhancing agents or compositions may be delivered over an extended period, e.g., 3-10 days, in an amount effective to produce at least an average daily dose of, e.g., 50 mg. Alternatively, the compositions can be formulated for controlled release, wherein the composition is administered once a day, once a week, or once a month. The compositions are typically administered for an extended period of time, for example, at least about 10 about, preferably at least about 30 weeks, more preferably at least about 60 weeks, and most preferably as long as the patient is receiving noticeable benefit from the treatment method.

In a preferred embodiment, the composition containing one or more neuro-enhancing agents is administered to an individual at a dose and for a period effective to produce an improvement in at least one criterion set forth as indicative of an improvement in the neurological disease, neurological defect or neurological age-related decline or impairment, such as an improvement in cognitive abilities, memory, motor skills, learning or the like, preferably an improvement is observed in at least two such criteria.

Criteria for assessing improvement in a particular neurological disease, neurological injury or age-related neurological change include methods of evaluating cognitive skills, motor skills, memory capacity or the like, as well as methods for assessing physical changes in selected areas of the central nervous system, such as magnetic resonance imaging (MRI) and computed tomography scans (CT) or other imaging methods. Such methods of evaluation are well known in the fields of medicine, neurology, psychology and the like, and can be appropriately selected to diagnosis the status of a particular neurological impairment. To assess a change in a neurological disease, neurological injury or age-related neurological change, the selected assessment or evaluation test, or tests, are given prior to the start of administration of the neuro-enhancing agents or compositions of the present invention. Following this initial assessment, treatment methods for the administration of the neuro-enhancing agents of the present invention are initiated and continued for various time intervals. At a selected time interval subsequent to the initial assessment of the neurological defect impairment, the same assessment or evaluation test (s) is again used to reassess changes or improvements in selected neurological criteria.

The compositions described herein can be administered in a variety of ways, such as orally, parenterally (e.g., subcutaneous, intravenous, intramuscular, intraarterial, intraperitoneal, intrathecal, intracardiac, or intrasternal), transcutaneously, transmucosally, subcutaneously, by inhalation, infusion, particularly via intracerebroventricular infusion, although oral administration is generally preferred. Depending on the route of administration, the compositions may be coated with or in a material to protect it from the natural conditions which may detrimentally affect its ability to perform its intended function. A particularly convenient method of administering compositions of the present invention is via oral administration.

A. Diseases and Disorders to be Treated

Neuro-enhancement resulting from the administration of the compositions described herein includes the stimulation or induction of neural mitosis leading to the generation of new neurons, i.e., exhibiting a neurogenic effect, prevention or retardation of neural loss, including a decrease in the rate of neural loss, i.e., exhibiting a neuroprotective effect, or one or more of these modes of action. The term "neuroprotective effect" is intended to include prevention, retardation, and/or termination of deterioration, impairment, or death of an individual's neurons, neurites and neural networks. Administration of the compositions described herein leads to an improvement, or enhancement, of neurological function in an individual with a neurological disease, neurological injury, or age-related neuronal decline or impairment.

Neural deterioration can be the result of any condition which compromises neural function which is likely to lead to neural loss, Neural function can be compromised by, for example, altered biochemistry, physiology, or anatomy of a neuron, including its neurite. Deterioration of a neuron may include membrane, dendritic, or synaptic changes which are detrimental to normal neuronal functioning. The cause of the neuron deterioration, impairment, and/or death may be unknown. Alternatively, it may be the result of age-, injury- and/or disease-related neurological changes which occur in the nervous system of an individual.

When neural loss is described herein as "age-related", it is intended to include neural loss resulting from known and unknown bodily changes of an individual that are associated with aging. When neural loss is described herein as "disease-related", it is intended to include neural loss resulting from known and unknown bodily changes of an individual which are associated with disease. When neural loss is described herein as "injury-related", it is intended to include neural loss resulting from known and unknown bodily changes of an individual which are associated with injury or trauma. It should be understood, however, that these terms are not mutually exclusive and that, in fact, many conditions that result in the loss of neural cells and/or neural connections can be related to age, disease and/or injury.

Some of the more common age-related neuropathies associated with neural loss and changes in neural morphology include, for example, Alzheimer's disease, Pick's disease, Parkinson's disease, vascular disease, Huntington's disease, and Age-Associated Memory Impairment. In Alzheimer's patients, neural loss is most notable in the hippocampus, frontal, parietal, and anterior temporal cortices, amygdala, and the olfactory system. The most prominently affected zones of the hippocampus include the CA1 region, the subiculum, and the entorhinal cortex. Memory loss is considered the earliest and most representative cognitive change because the hippocampus is well known to play a crucial role in memory. Pick's disease is characterized by severe neural degeneration in the neocortex of the frontal and anterior temporal lobes which is sometimes accompanied by death of neurons in the striatum. Parkinson's disease can be identified by the loss of neural cells in the substantia nigra and the locusceruleus.

Huntington's disease is characterized by degeneration of the intrastriatal and corticalcholmergic neural cells and GABA-ergLc neural cells. Rarkmson's and -Huntington's diseases are usually associated with movement disorders, but often show cognitive impairment (memory loss) as well.

Age-Associated Memory Impairment (AAMI) is another age-associated disorder that is characterized by memory loss in healthy, elderly individuals in the later decades of life. Presently, the neural basis for AAMI has not been precisely defined. However, neural death with aging has been reported to occur in many species in brain regions implicated in memory, including cortex, hippocampus, amygdala, basal ganglia, cholinergic basal forebrain, locus ceruleus, raphe nuclei, and cerebellum.

Animal Models for Evaluating Neurogenesis and/or Reducing Expression of Beta-Amyloid Aging rodent brains do not develop senile plaques and neurofibrillary tangles. Most recent studies suggest, however, that loss or shrinkage of neurons, dendrites, and/or synapses is more closely correlated with either dementia or aging than are plaques and tangles. Aging rats exhibit neural cell loss in the pyramidal cells of the hippocampus, especially in field CA1, as well as cell loss or dendritic/synaptic changes in some other brain regions. Moreover, aging rodents show extensive hippocampalastrocyte hypertrophy just as do aging humans. In addition, loss of neural cells in field CA1 of the hippocampus is a consistent correlate of aging across species, and is also prominent in human neurodegenerative diseases, such as Alzheimer's disease. For these reasons, the study of neural loss in aging rats, for example, is predictive of general mechanisms of brain aging and associated neural loss in humans due to diseases such as Alzheimer's diseases.

Animal models, such as the models described in U.S. Pat. No. 5,939,407 and Haughey et al., *J. Neurochem.* 83: 1509-1524 (2002), represent improvement in models for age-associated disease and decline because they relate to an intact animal, which is generally preferred over tissue culture models. Further, the animal model described in U.S. Pat. No. 5,939,407 employs a strain of rat that was developed by the National Institute on Aging as a premier model of mammalian aging. The particular rat strain (Brown Norway/Fischer 344 F1 cross rats) was selected due to its normal pattern of aging, with few indications of abnormal pathology. This strain also loses neural cells in field CA1 of the hippocampus with aging and exhibits memory loss. This system represents one of the most natural animal models of neural degeneration and/or deterioration because it reflects a gradual loss of neural cells. Furthermore, the neural loss is not provoked by experimental intervention or abnormal pathology. Its brain aging pattern is also highly analogous to human and other mammalian species brain aging patterns.

In one embodiment, an animal model can be used to evaluate the effect of a neuro-enhancing agent in beta-amyloid expression and/or neurogenesis in an animal transgenic for Alzheimer's disease. Suitable models include the animal model described by Borchelt et al. (1996) *Neuron* 17: 1005-1013 and Haughey et al. (2002) *J. Neurochemistry* 83: 1509-1524. Male mice (12-14 months old) overexpressing a mutant form of amyloid precursor protein (APP) are maintained on a 12 hour light/12 hour dark cycle with free access to food and water. This line of mice exhibits increased levels of soluble amyloid beta protein and develops amyloid deposits in an age-dependent manner with diffuse deposits first appearing at about 12 months of age and plaque-like deposits developing later, typically by 18-22 months of age. To determine proliferation and survival of NP/SC in the dentate gyms in the absence and presence of 3α-hydroxy-5α-pregnan-20-one (THE), mice are given five daily injections of 5-bromo-2' deoxyuridine (BruU; 50 mg/kg, i. p.). 12 experimental mice and six control mice are used to assess the effects of 3α-hydroxy-5α-pregnan-20-one (THP) on the formation of amyloid deposits. The 12 experimental mice are also given daily injections of 3α-hydroxy-5α-pregnan-20-one (THP) (6 mice are given 10 mg/kg THP and 6 mice are given 100 mg/kg THP) for one week, two weeks and 4 weeks prior to the injections of 5-bromo-2' deoxyuridine (BruU). The six control mice are given daily injections of a saline solution contained in the same volume as the volume given to the experimental mice. All mice are sacrificed 12 days following the injections of BruU.

Brain sections from experimental and control mice are prepared and compared for incorporation of BruU. For the quantification of neuro-enhancement, immunopositive cells in the dentate gyms from three sections in each of the 12 experimental and six control mice are counted and compared. Rate of cell division is usually determined using nucleotide (BrDU (bromodeoxy-uridine, or 3H-thymidine) incorporation into DNA. The ratio of the BrDU or 3H-thymindine labeled cells vs. non-labeled cells will indicate the dividing speed. DNA incorporation into cells is not only present in dividing cells but also occurs during DNA repair thereby generating the potential of a false positive by counting the mismatch DNA repair cells which also incorporate a relative high amount BRDU or 3H thymidine. To circumvent this source of BrDU incorporation, the MuLV-enhanced green fluorescent protein (GFP) is used to label the dividing cells. The cell proliferation rate will be determined by measuring the ratio of OFF expression cell vs. non-GFP expression cells by FACS. Murine leukemia virus (MuLV) has been demonstrated to only infect cells during mitosis but not to infect non-dividing cells (Lewis and Emennan 1994). Moreover, this strategy has been successfully used in the labeling of the dividing neurons in vitro and in vivo (van Praag, H., Schinder, A. F., Christie, B. R., Toni, N., Palmer, T. D., Gage, F. H., Functional neurogenesis in the adult hippocampus. *Nature.* 2002.415, p 1030-1034.) The infected cells can express GFP stably which makes it possible to follow neurons that have divided in vivo as they differentiate and migrate to sites within the brain. In addition, MuLV infection-GFP strategy permits a more precise comparison of the dividing speed between the THP treated cells and the non-treated cells by FACS analysis. Furthermore, this use of the retroviral infection strategy may also provide data for future application for future gene therapy purposes.

In these experiments, a strain of virus was used in which the GFP was inserted in frame with the authentic start codon of the internal ribosome entry site-transgene cassette which is positioned between the env gene and the 3' long terminal repeat. This virus vector exhibited replication kinetics similar to those of the wild-type MuLV and mediated efficient delivery of transgene (Logg, C. R. Tai, C. K. Logg, A. Anderson, W. F. Kasahara, N., A uniquely stable replication-competent retrovirus vector achieves efficient gene delivery in vitro and in solid tumors. *Human Gene Therapy.* 2001.8: p 921-932).

Neural loss through disease, age-related decline or physical insult leads to neurological disease and impairment. The compositions described herein can counteract the deleterious effects of neural loss by promoting development of new neurons, new neurites and/or neural connections, resulting in the neuroprotection of existing neural cells, neurites and/or neural connection, or one or more these processes. Thus, the neuro-enhancing properties of the compositions described herein provide an effective strategy to generally reverse the neural loss associated with degenerative diseases, aging and physical injury or trauma.

The administration of 3α-hydroxy-5α-pregnan-20-one, or a substantially equivalent variant molecule, to an individual who is undergoing or has undergone neural loss, as a result of a disease, defect or age-related decline, can generally provide an effective therapeutic strategy for the treatment of neurological conditions caused by neural loss. The defects and diseases that can benefit from administering the agents, compositions and methods of the present invention include, but are not limited to, spinal cord injury, stroke, head injury, epilepsy, Parkinson's disease and Alzheimer's disease. Moreover, given that 3α-hydroxy-5α-pregnan-20-one, and substantially equivalent variant molecules, possess neuro-enhancing activities, these agents and compositions may also be administered to improve age-related memory and learning impairments.

The examples demonstrate that administration of α-hydroxy-5α-pregnan-20-one or tetrahydroprogesterone (THP or APα) reverses the learning deficits of mice transgenic for Alzheimer's diseases (3×TgAD mice). The data indicate that at 3 months, 3×TgAD mice exhibit a learning deficit relative to the performance of normal non-Tg mice. In the normal high functioning non-Tg mice, with a concomitant high level of neurogenesis, APα did not augment the learning performance. In contrast, APα significantly increased the learning performance of 3×TgAD mice to a level comparable to non-Tg mice such that the performance of APα treated 3×TgAD mice was not statistically different from the normal non-Tg mouse. One week following the learning trial, mice were tested for memory of the learned association. Non-Tg mice exhibited slightly less than 50% of the conditioned response compared to a 28% response rate of 3×TgAD mice. APα did not significantly augment the memory performance of non-Tg mice. However, APα treated 3×TgAD mice exhibited a significant increase in memory to a level comparable to the normal non-Tg mice.

As also shown in the examples, 3α-hydroxy-5α-pregnan-20-one or tetrahydroprogesterone (THP), a naturally occurring metabolite of progesterone, was found to induce or stimulate the formation of new hippocampal neurons. Results of these analyses demonstrate that the number of mitotic neural cells was approximately doubled in the presence of tetrahydroprogesterone.

Without being bound by any one theory, it is hypothesized that the neuro-enhancing agents described herein act through neural progenitor and/or stem cells (NP/SC). In certain regions of the brain of adult mammals, small populations of NP/SC are found that are capable of dividing and differentiating into neurons and glial cells. Moreover, it is the NP/SC populations of neural cells that respond to changing environmental demands, including brain injury and incipient neurological disease states, by increasing their proliferation and/or survival. Additionally, the rate of NP/SC proliferation is reduced in aged populations, leading to memory and learning impairments. Transplantation of NP/SC, however, has been shown to reverse age-associated memory impairment. Recently, amyloid beta protein, a protein implication in the onset of Alzheimer's disease, has been shown to alter the proliferation and differentiation of NP/SC, which suggest a role for perturbed NP/SC behavior in the pathogenesis of Alzheimer's disease.

The precise signals that influence neural progenitor cell fate are currently beginning to be identified. The data presented herein, however, are suggestive of a mechanism whereby the neuro-enhancing agents signal neural progenitor and/or stem cells to divide. In this context, the neuro-enhancing agents of the present invention belong to a class of neural expansion signals. Neural expansion signals can provide for the growth of new neurons by causing a neural progenitor and/or stem cells to divide without exhausting the existing population of NP/SC. Thus, the neuro-enhancing agents of the present invention may be critically important to combat the effects of neurodegenerative disease and age-related mental decline and disability. Further, the neuro-enhancing agents described herein may induce or stimulate NP/SC to divide by modulating calcium and/or phosphate levels and/or homeostasis, and/or by restoring dysregulated calcium to normal levels. Changes in intracellular calcium and/or states of protein phosphorylation can also protect against neural loss, and thereby act to protect neurons from apotosis or other like processes leading to cell death. Finally, although certain progesterone metabolites, such as 3α-hydroxy-5α-pregnan-20-one, are known to be neuroactive steroids that act as positive allosteric modulators of gamma-aminobutyric acid A (GABAA) receptor complexes, this may or may not be the mechanism of action from NP/SC.

The examples also demonstrate that the administration of 3α-hydroxy-5α-pregnan-20-one (THP) reduces age-related β-amyloid expression. The development of intraneuronal beta amyloid is typically seen in 6 and 9 month old animals and the development of plaques in 12 month old animals. Plaques are rarely seen in 9 month old animals. THP (10 mg/kg/week, administered once a week for 6 months) was administered to 9- and 12-month male mice transgenic for Alzheimer's disease (3×Tg-AD). The 9 month old animals were started on APα at 3 months of age prior to the development of beta amyloid accumulation in the whereas the 12 month old animals were started on APα at 6 months of age when beta amyloid had already begun to accumulate within neurons. The results indicate that administration of THP significantly decreased the amount of beta amyloid in the cerebral cortex of male mice transgenic for Alzheimer's disease. Western Blot analysis showed a form of beta amyloid termed Abeta*56, which is the oligomer (multiple amyloid beta peptides joined together) that, in animal studies, leads to memory loss in both transgenic Alzheimer mouse models and in rats injected with Abeta*56. In the 12 month old animals, the level of Abeta*56 was much lower, likely due to the development of beta amyloid plaques in these animals, which reduces the amount of Abeta*56. Immunocytochemical detection of beta amyloid showed that administration of APα substantially decreases Abeta*56 in hippocampal neurons. APα also decreases the immunoreactivity of phosphorylated tau, which is the basis for neurofibrillary tangles.

The compositions described herein may also be effective for the treatment of neural damage caused by therapies aimed at combating certain cancers that affect the brain. For instance, cranial radiation therapy is crucial to the successful treatment of many primary brain tumors, cancers metastatic to the brain, CNS involvement of leukemia/lymphoma, and head and neck cancers. Such irradiation that involves the cerebrum causes a debilitating cognitive decline in both children and adults. Experiments have shown that hippocampus-dependent learning and memory are strongly influenced by the—activity of neural progenitor- and/or stem cells and their—proliferative progeny. Since the hippocampal granule cell layer undergoes continuous renewal and structuring by the addition of new neurons, radiation at much lower does than that needed to injure the more resistant post-mitotic neurons and glia of the brain, has been found to affect these highly proliferative progenitors and/or stem cells severely. The progenitor and/or stem cell, therefore, is considered to be so sensitive to radiation that a single low dose to the cranium of a mature rat is sufficient to ablate hippocampal neurogenesis. Recent experiments have further found that progressive learning and memory deficits following irradiation may be caused by the accumulating hippocampal dysfunction that results from a long-term absence of normal progenitor and/or stem cell activity. See. Monje and Palmer (2003) *Current Opinions in Neurology* 16 (2): 129-134. Thus, given the neurogenic effect compositions described herein on hippocampal cell cultures, therapeutic methods utilizing these compositions may benefit individuals who are undergoing or have undergone radiation therapy for brain-related cancers.

IV. Kits

The compositions described herein can be packaged in kit. The kit can include a single dose or a plurality of doses of a composition containing one or more neuro-enhancing agents, and instructions for administering the compositions. Specifically, the instructions direct that an effective amount of the composition be administered to an individual with a particular neurological disease, defect or impairment as indicated. The composition can be formulated as described above with reference to a particular treatment method and can be packaged in any convenient manner.

The instructions can be affixed to the packaging material or can be included as a package insert. While the instructions typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions. Embodiments of the present invention also include the use of the above-described pharmaceutical products for the treatment of a human patient with a neurological disease, neurological defect or age-related neurological decline or impairment.

The following examples are put forth so as to provide those of ordinary skill in the art with a complete disclosure of how to make, to use and to evaluate the therapeutic agents, compositions and methods of the present invention, and are not intended to limit the scope of what is regarded as the invention. Efforts have been made to ensure accuracy with respect to numbers presented (e, g, amounts, concentrations, etc.), but some experimental errors and deviations should be allowed for.

EXAMPLES

Materials and Methods

The animals studies described below for evaluating neurogenesis and/or reduction of beta-amyloid expression were done using a triple transgenic Alzheimer's disease mouse model (3×TgAD). The 3×TgAD mouse carries mutations (APPSwe, PS1M146V and tauP301L) of three human familial AD genes and manifests age-dependent neuropathology of both β-amyloid plaque formation and neurofibrillary tangles. In addition to expressing neuropathological markers of AD, the 3×TgAD mouse exhibits learning and memory deficits as early as 4 months, but not 2 months. The 3×TgAD, homozygous mutant of human APPswe and tauP301L and PS1M146V and its background (129/Sv×C57BL/6) were obtained from Dr. Frank Laferla (UC Irvine) and the colonies were established at USC. The characterization of amyloid and tau pathologies and synaptic dysfunction in this line of mice has been described previously and confirmed in our laboratory.

Using this AD model, the following were assessed: 1) THP concentration, neurogenic and cognitive status at 3 months of age; 2) impact of THP on both neurogenic and cognitive status using unbiased stereology, phenotype immuncytochemistry, real-time RT-PCR, Western blot, and eyeblink trace conditioning training and memory.

Example 1

The effect of 3α-hydroxy-5α-pregnan-20-one (THP) on hippocampal neural cells

Hippocampal neural cells were obtained from an embryonic day 18 rat hippocampus, ~12,000 neurons/sample. The sample was 95% neuronal. No selection for neuronal subtypes was conducted. Hippocampal neurons were treated with 3a-hydroxy-5a-pregnan-20-one (THP). 3α-hydroxy-5α-pregnan-20-one (THP) was added to two samples containing hippocampal neural cells at a concentration of either 10 nanomolar (nM) and 100 nanomolar (nM). The cells were incubated for 24 hrs at 37° C. Neurons were grown in a defined medium, Neurobasal+B27 supplement in the absence (control) or presence of THP or other test molecule (experimental). The samples with added THP were compared with a control sample containing only hippocampal neural cells. Changes in the mitotic appearance of the neural cells were observed. A mitotic appearance of a particular neural cell is defined as a doublet form in the cell body of the neural cell. The doublet form is indicative of a neural cell undergoing mitosis. A graphic comparison among the three samples studied is shown in FIG. 1. These data reveal that there is an approximate 2 fold increase in the mitotic phenotype of the neural cells studied at either 10 nm THP or 100 nm THP, as compared with the control sample. Data are expressed as percent of the total number of neurons exhibiting mitotic phenotype, mean+SEM, $p<0.01$, *$p<0.001$.

Figure 2:
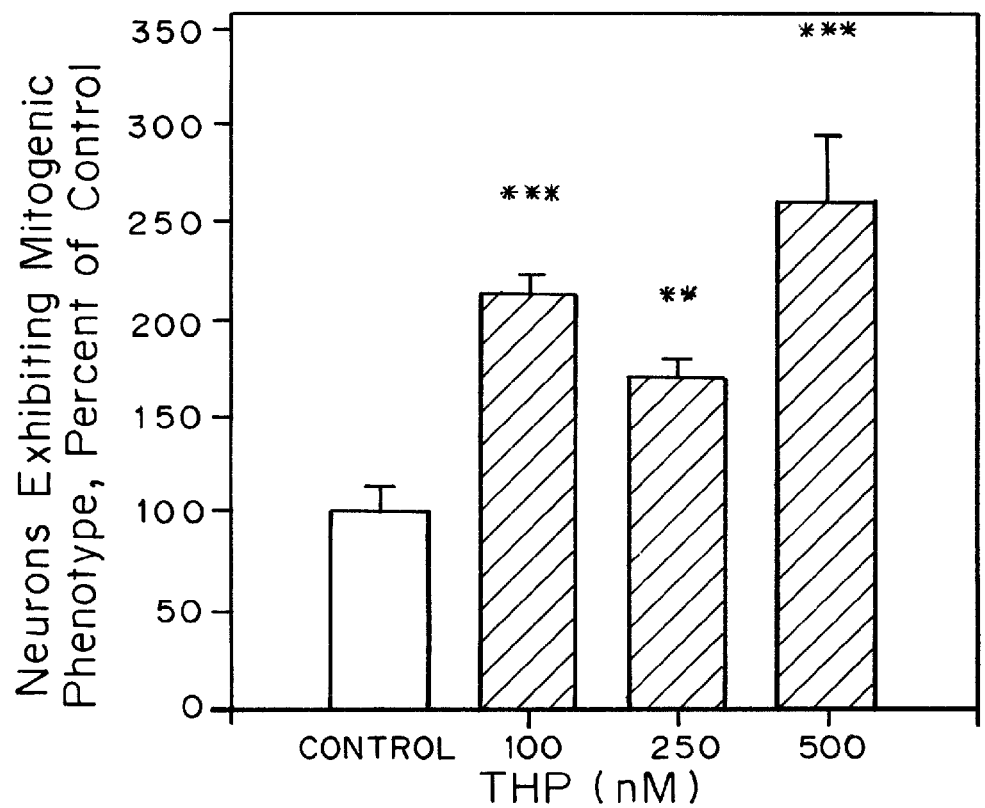
FIG. 2 is a graph showing the effect of 3α-hydroxy-5α-pregnan-20-one (THP) concentration (nM) on hippocampal neurons relative to the number of control neurons with a mitotic appearance, where mitotic appearance was defined as a double cell body indicative of mitosis.

The experiment described above was repeated only THP was added to three samples containing hippocampal neural cells at a concentration of 100 nanomolar (nM), 250 nM and 500 nM. The samples with added THP were compared with a control sample containing only hippocampal neural cells. A graphic comparison among the four samples studied is shown in FIG. 2. These data reveal that there is an approximate 2-3 fold increase in the mitotic phenotype of the neural cells studied, as compared with the control sample. The greatest effect in induction of the mitotic phenotype was observed at 500 nm THP. Data are expressed as percent of mean+SEM, $p<0.01$, *$p<0.001$.

Example 2

Effect of 3α-hydroxy-5α-pregnan-20-one (THP) on the expression of cell proliferating markers THP also was shown to increase the expression of cell proliferating markers. Expression of cell cycle proteins have been successfully used to evaluate cellular proliferation. One such protein is the nuclear proliferation protein, Ki-67, which is expressed during the G1, S, G2, and M phases of the cell cycle, but is not expressed during the Go (resting) phase. Because Ki-67 antigen has a short half-life, it can be used as a marker of actively proliferating cells. Another cell cycle protein is cell division control protein 2 (cdc2) which is a cyclin dependent kinase (also called CDK1) which plays a crucial role in the G1/S and G2/M phase. If THP induces neuronal proliferation, cell proliferation markers should be elevated.

Figure 3:
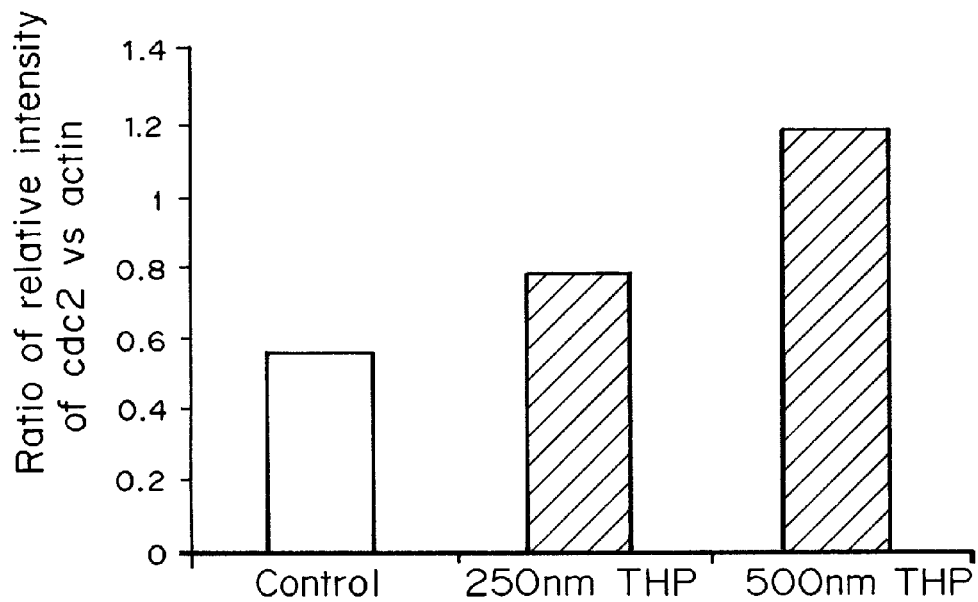
FIG. 3 is a graph showing the effect of 3α-hydroxy-5α-pregnan-20-one (THP, nM) on the expression of cell division of control protein 2 (cdc2) in hippocampal neurons; neurons were collected following 24 hrs of THP exposure.

Hippocampal neurons were treated with THP at a concentration of 250 nM for 72 hours and immunostained with antibodies for the nuclear proliferation marker, ki-67 antigen, which appears yellow. The results indicate that THP induces the expression of the nuclear proliferation marker Ki-67. This is supported by the fact that the cytoplasm of the donor and the daughter cells did not completely separate. The cell cycle protein cdc2 is also observed in a dose dependent fashion (see FIG. 3). As shown in the figure, THP increases expression of cell division control protein 2 (cdc2) in hippocampal neurons.

For this experiment, neurons were collected following 24 hrs of THP exposure. Forty μg protein of the total cell lysate was loaded and separated by 12% SDS-gel using antibody (Ahcom) specifically against cdc2- and analyzed using Un-Scan-It image software (Ilk Scientific Corp.). This figure shows a representative Western blot from one of three different experiments which have the similar results.

Example 3

Effect of 3α-hydroxy-5α-pregnan-20-one (THP) on the production of neurons

Figure 4:
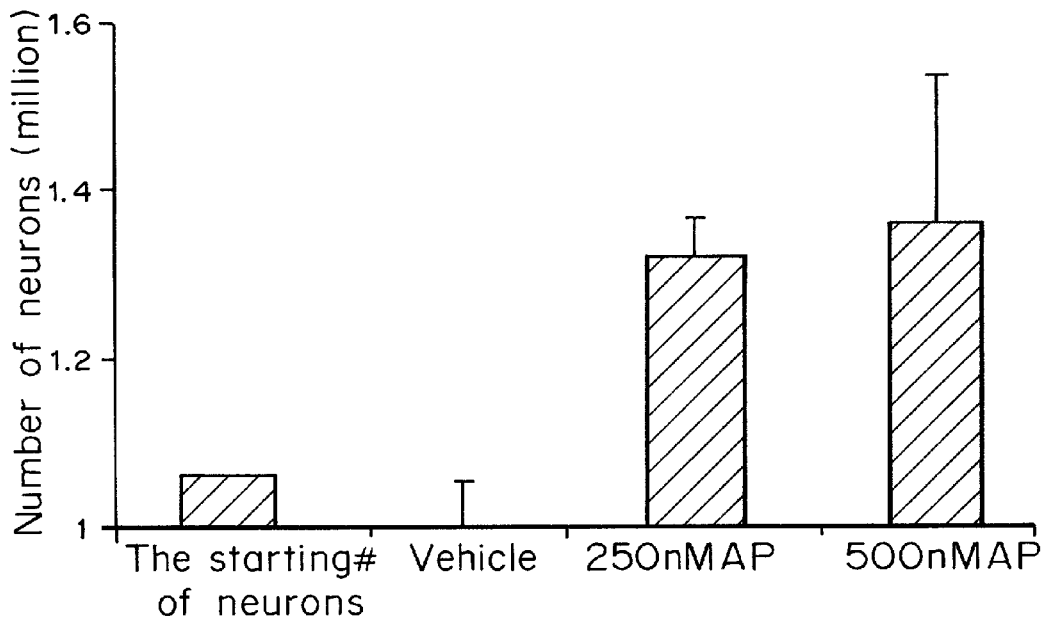
FIG. 4 is a graph showing the effect of 3α-hydroxy-5α-pregnan-20-one (THP, nM) on the total number of hippocampal neurons.
Figure 5:
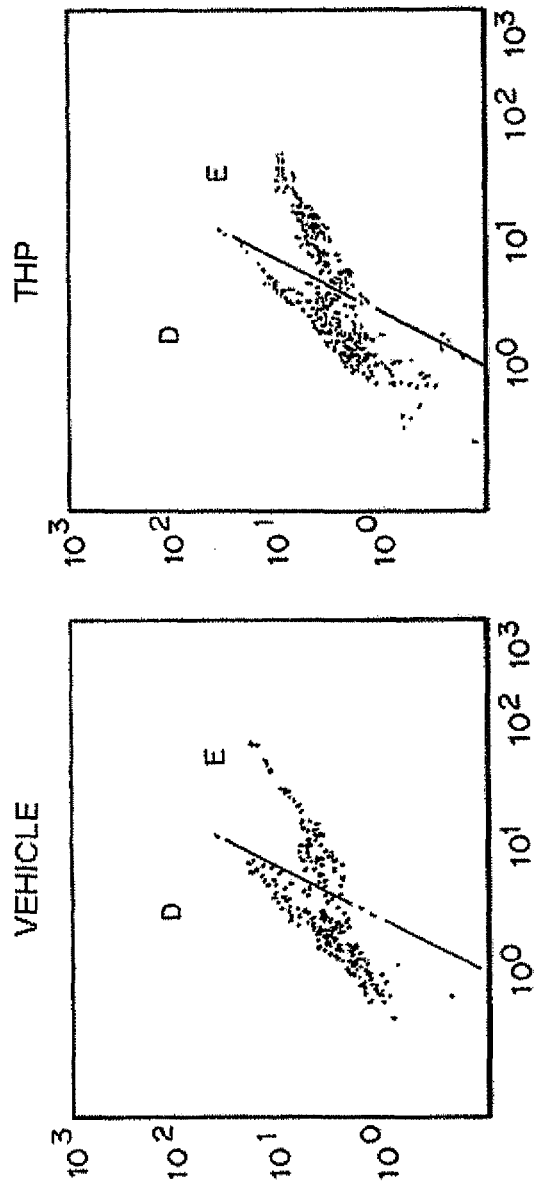
FIG. 5 is a graph showing the effect of 3α-hydroxy-5α-pregnan-20-one (THP) on neuron number as assessed in MuLV-GFP infected mouse neurons; the effect of THP on HT-22 cells proliferation was detected on MuLV infected cells; left panel shows the FACS profile of vehicle; right panel shows the FACS profile of THP treated MuLV-GFP infected cells; the accompanying table (Table 1) summarizes the FACS results. V=vehicle; THP (250 nM).

Having determined that THP increases the expression of the cell proliferating markers, a determination was sought as to whether the increase in cell proliferation markers translated into an increase in neuronal number. It was found that THP induced neuronal proliferation by increasing the total cell number and the dividing speed. As shown in FIG. 4, THP increased the neuron number by approximately 30%. These results are highly consistent across different experiments and are also comparable to the results obtained using the mouse hippocampal neuron cell line (HT-22) (FIG. 5 and Table 1 below). As shown in FIG. 5 and Table 1, THP increases neuron number as assessed in MuLV-GFP infected mouse neurons. The effect of THP on HT-22 cells proliferation was detected on MuLV infected cells. The left panel shows the FACS profile of the vehicle. The right panel shows the FACS profile of THP treated MuLV-GFP infected cells.

The table summarizes the FACS results. V=vehicle; THP (250 nM). THP treatment increased the dividing cell number 22% as determined by fluorescent associated cell sorting (FACS). Therefore, the data demonstrate that THP can increase the proliferation of neuronal cells either in primary cultured cells or continuous cell lines, from rat and mouse.

Example 4

Effect of 3α-hydroxy-5α-pregnan-20-one (THP) on 3H-thymidine uptake

Figure 6:
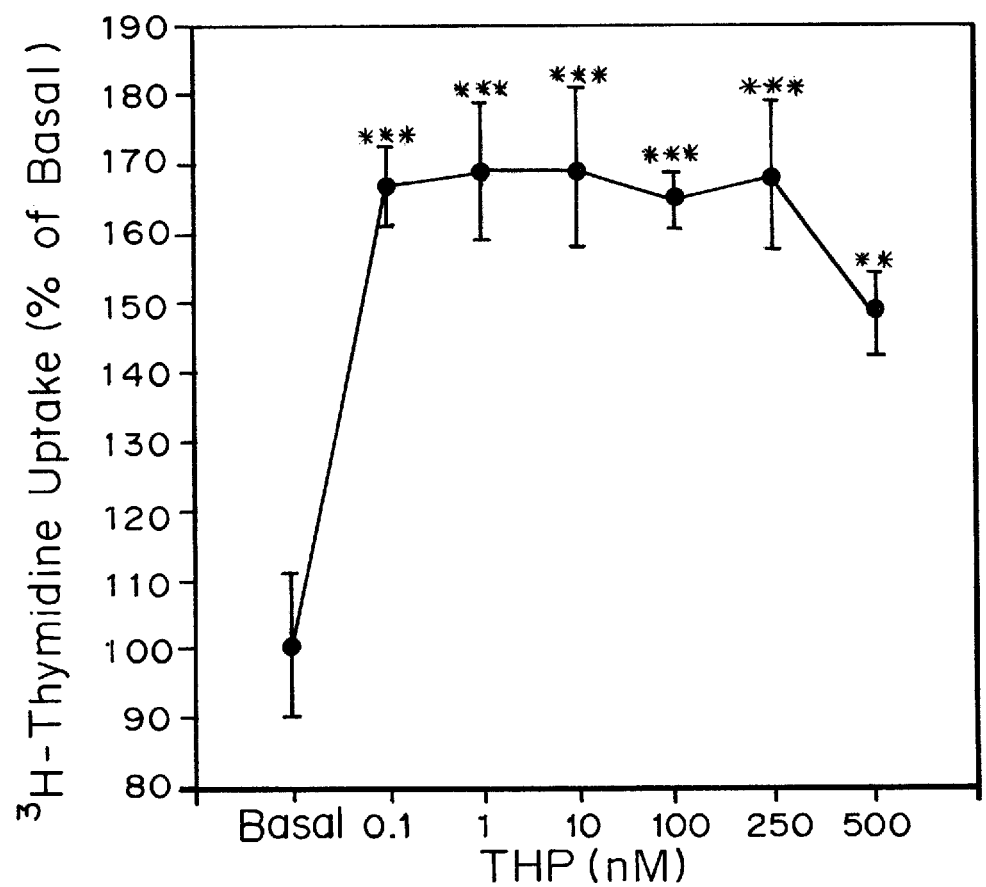
FIG. 6 is a graph showing the dose response of 3α-hydroxy-5α-pregnan-20-one (THP, nM) administration on 3H-thymidine incorporation in hippocampal neural cells as measured by 3H-thymidine incorporation (% of Basal).
Figure 7:
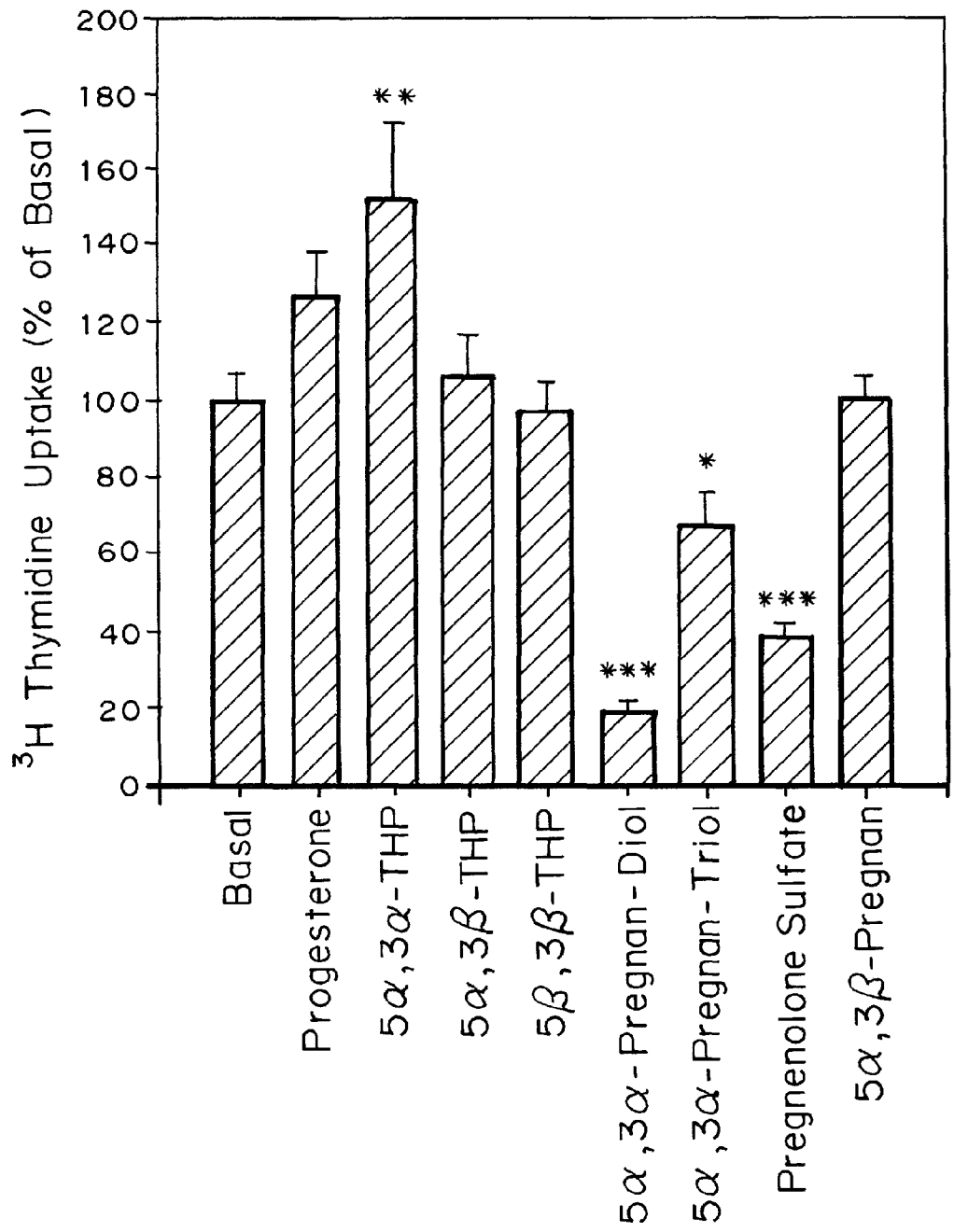
FIG. 7 graphically depicts the steroid specificity of 3α-hydroxy-5α-pregnan-20-one (THP), as compared to other structurally and chemically similar steroids by measuring the THP-induced 3H-thymidine incorporation in hippocampal neural cells.

Biochemical analyses of 3H-thymidine uptake, as a measure of DNA synthesis, were used as the experimental vehicle to confirm the morphological observations described in examples 1 and 2. As shown in FIG. 6, THP induced a 80% increase in 3H-thymidine uptake relative to control ($F=12.31$, df 3, 19, $p<0.0001$) from about 0.1 nm THP to about 250 nm THP. Thus, the range for the neurogenic effect of THP on neural cells is quite is sensitive and quite broad. Furthermore, DNA synthesis is specifically induced in the presence of THP ($F=9.15$, df6, 27, $p<0.0001$), as compared with other structurally and chemically similar steroids, as shown in FIG. 7.

For these experiments, cultured hippocampal neural cells, derived from embryonic day 18 rat fetuses, were allowed to adhere to polylysine coated plastic cover-slips for 40 min in serum containing medium. Following adhesion, neurons were exposed to 1 Ci/ml 3H-thymidine in the presence or absence of 100-500 nM THP and allowed to incubate at 37° C. for 24 hours in the absence or presence of the indicated steroids. Data are expressed as mean+SEM, *$p<0.05$, $p<0.01$, *$p<0.001$. The results demonstrated that THP induction of 3H-thymidine incorporation is highly specific. Progesterone induced a modest increase in 3H-thymidine incorporation, however, the stereoisomers of THP, i.e., 5 cc, 3ss-THP and 5ss, 3ss-THP, as well as 5α,3P-pregnen showed no effect.

Additionally, 5α,3α-pregnan-diol; 5α,3α-pregnan-triol and pregnenolone sulfate (PS), which are known to increase morphological differentiation, induced a significant decrease in 3H-thymidine incorporation which is consistent with their differentiation effect. The steroid specificity analysis provides evidence for the specificity of THP-induced mitogenesis. Moreover, consistent with this evidence is the observation that differentiation factors have an effect opposite to that of THP in that these agents cause a decrease in 3H-thymidine incorporation.

Figure 8:
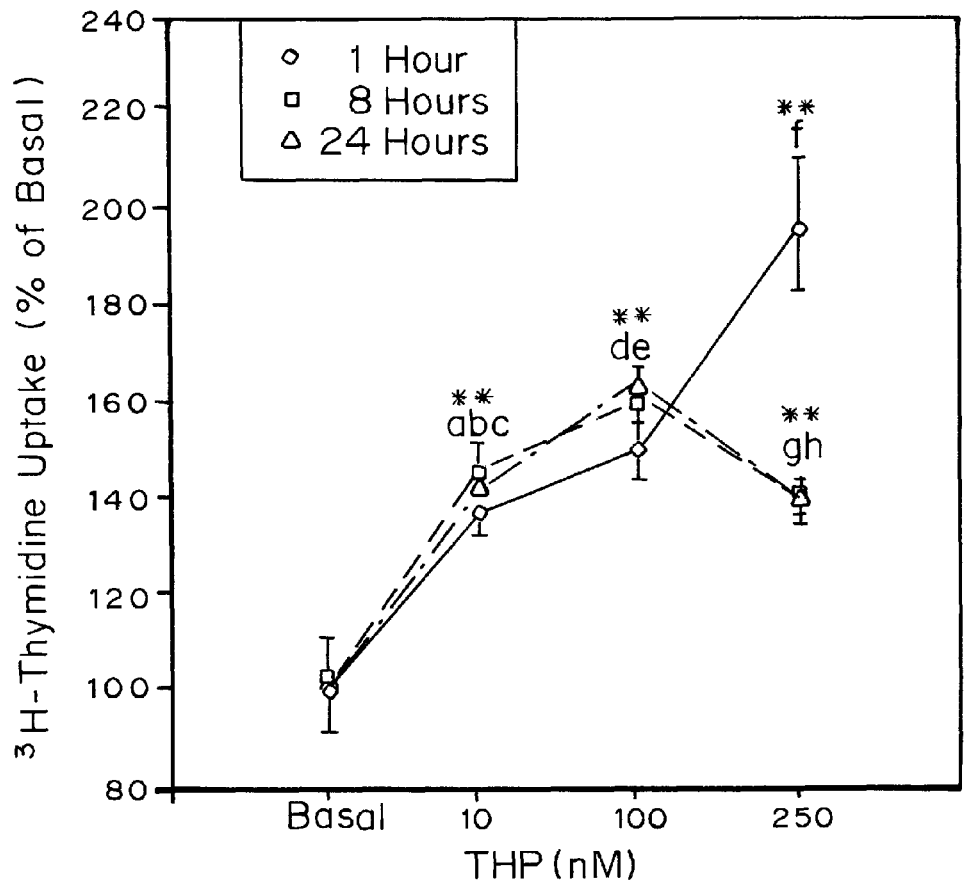
FIG. 8 depicts the time course of 3α-hydroxy-5α-pregnan-20-one (THP)-induced 3H-thymidine incorporation (% of basal) in hippocampal neural cells at 1 hour, 8 hour and 24 hour time intervals.

The time course of THP-induced 3H-thymidine incorporation in hippocampal neuronal cells is shown in FIG. 8 where cultured hippocampal nerve cells, derived from embryonic day 18 rat fetuses, were allowed to adhere to polylysine coated plastic cover-slips for 40 min in serum containing medium. Following adhesion, serum containing medium in the presence or absence of 10-250 nM THP plus 1 pCi/ml 3H-thymidine and allowed to incubate at 37 for 1, 8 or 24 hours. Data are expressed as mean±SEM, *$p<0.05$, $p<0.01$, *$p<0.001$.

Example 5

Figure 9:
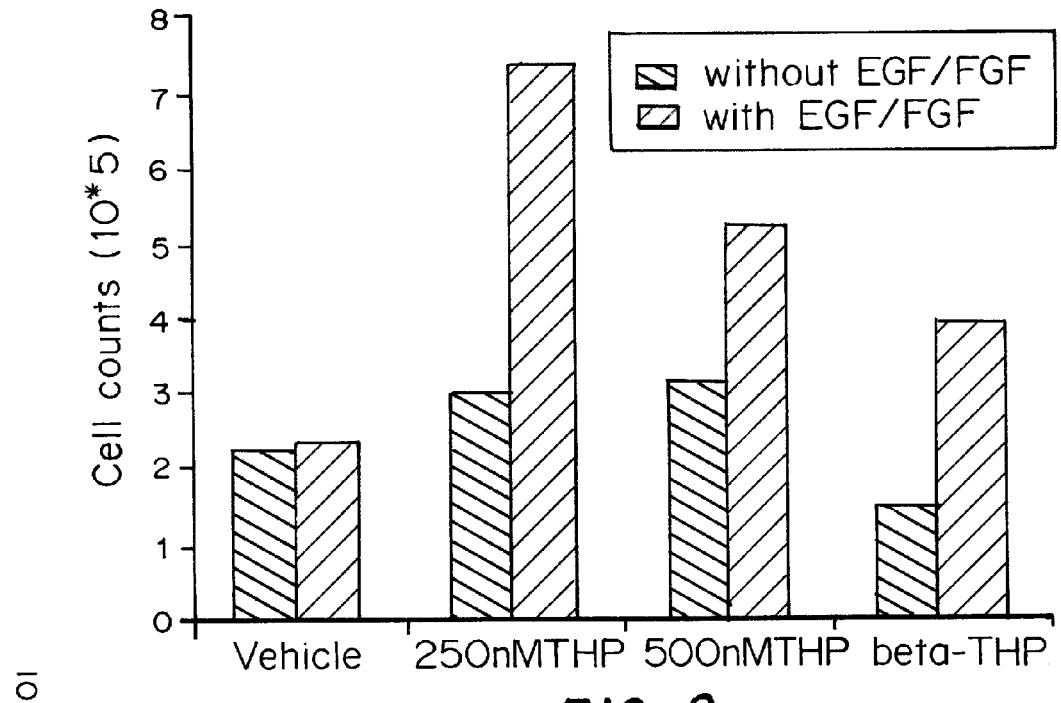
FIG. 9 shows the effect of 3α-hydroxy-5α-pregnan-20-one (THP) administration on rat neural stem/progenitor cell growth.

Effect of 3α-hydroxy-5α-pregnan-20-one (THP) on the production of neural stem cells Experiments to determine whether THP promotes neural stem cells growth were also performed. In FIG. 9, neural spheres were generated from the periventricular are and hippocampus of embryonic day 18 rat embryos. 5 rat embryos were treated with THP alone or with EGF and FGF-2 as mitogens. The approximately third passage of neural spheres were collected and randomly disturbed evenly to each dish. Dishes were treated with reagents as labeled in the absence of progesterone for 36 hours. Cells were then collected and trypsinized in to single cells. The cell numbers were counted blind using a hemacytometer and plotted in Excel.

Figure 10:
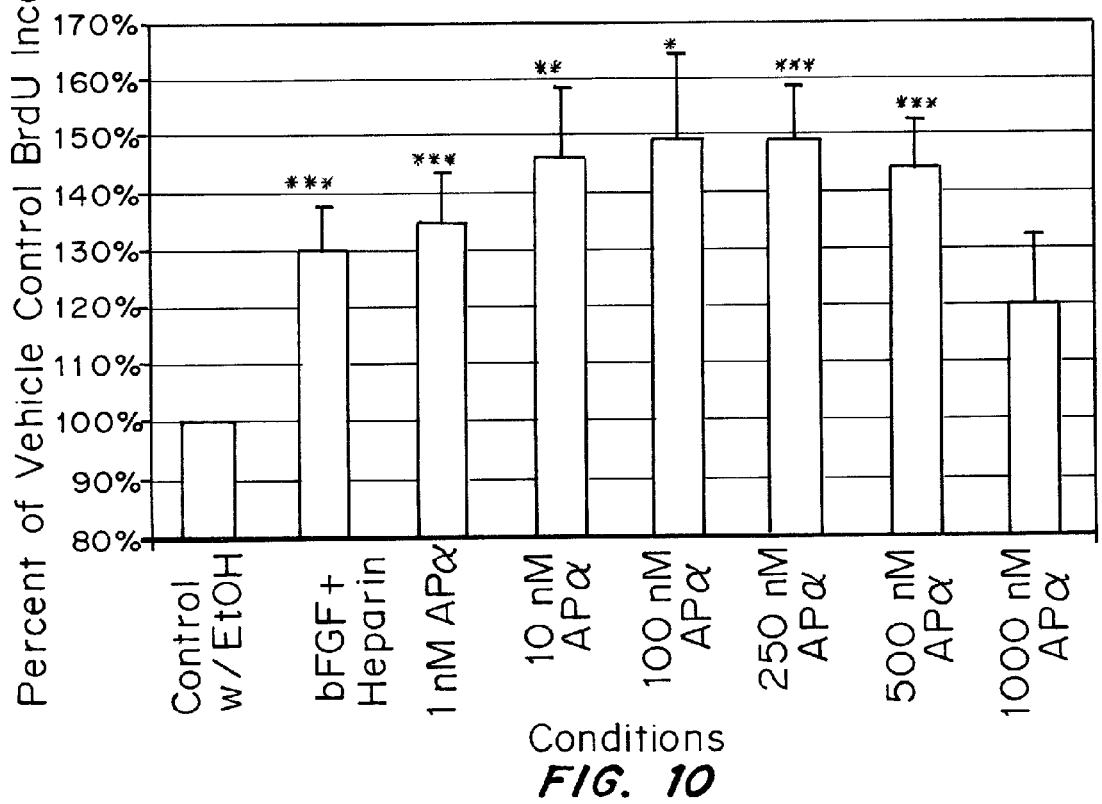
FIG. 10 is a graph showing the effect of 3α-hydroxy-5α-pregnan-20-one (THP, nM) on the proliferation of human neural stem cells.

Another experiment was performed to assess the neurogenic effects of THP administration on human neural stem cells. The results are shown in FIG. 10. In this experiment, neural stem cells derived from human fetal cortex were treated with varying concentrations of APα [1-1000 nM] or with bFGF [20 ng/ml]+heparin [511 lg/ml] as a THP positive control. The proliferation marker, BrdU [10 uM] was added simultaneously with test molecules and the cells were incubated at 37° C. for 24 hours. Quantitative Elisa chemiluminescence of BrdU signal was conducted at 24 hrs following addition of substrate and chemiluminescence determined by LMax microplate luminometer (Molecular Devices) (Roche Diagnostics Corp., Cell Proliferation ELISA, BrdU (chemiluminescence). THP at 250 and 500 nM, significantly increased BrDU chemiluminescence relative to vehicle control condition and was consistently greater than the positive control bFGF+heparin. Data are presented as mean±SEM and are derived from three separate experiments.

Example 6

Evaluation of the effect of 3α-hydroxy-5α-pregnan-20-one (THP) on the proliferation and survival of NP/SC in the dentate gyrus An aged population of mice is assessed at various time intervals for the effects of the treatment methods described herein. The particular rat strain (Brown Norway/Fischer 344 F1 cross rats) was selected as such a model due to its normal pattern of aging, with few indications of abnormal pathology. Experimental treatment methods include administering one or more of the neuro-enhancing agents of the present invention to a set of aged mice, as compared to mice from the same population who are not receiving treatment methods of the present invention.

For example, 12 experimental mice are given daily injections of 3α-hydroxy-5α-pregnan-20-one (THP) (6 mice are 10 mg/kg THP and 6 mice are given 50 mg/kg THP) for a selected time interval for treatment. The control mice are given daily injections of a saline solution contained in the same volume as the volume given to the experimental mice. Treatments regimens are continued for 2 week, 1 month, 3 months and 6 months time intervals. At the end of the selected time period for treatment, proliferation and survival of NP/SC in the dentate gyms in the absence and presence of 3α-hydroxy-5α-pregnan-20-one (THP) is determined. To assess neurological differences between the experimental and control mice, all mice are given five daily injections of 5-bromo-2'deoxyuridine (BruU; 50 mg/kg, i. p.). All mice are sacrificed 12 days following the injections of BruU. Brain sections from experimental and control mice are prepared and compared for changes in generation and survival of neural cells.

For the quantification of neuro-enhancement, immunopositive cells in the dentate gyrus are from three sections in each of the experimental and control mice are counted and compared. DNA incorporation into cells is not only present in dividing cells but also occurs during DNA repair thereby generating the potential of a false positive by counting the mismatch DNA repair cells which also incorporate a relative high amount BRDU or 3H thymidine. To circumvent this source of BrDU incorporation, the MuLV-enhanced green fluorescent protein (GFP) was used to label the dividing cells. The cell proliferation rate will be determined by measuring the ratio of GFP expression cell vs. non-GFP expression cells by FACS. Murine leukemia virus (MuLV) has been demonstrated to only infect cells during mitosis but not to infect non-dividing cells (Lewis and Emerman 1994). Moreover, this strategy has been successfully used in the labeling of the dividing neurons in vitro and in vivo (van Praag, H., Schinder, A. F., Christie, B. R., Toni, N., Palmer, T. D., Gage, F. H., Functional neurogenesis in the adult hippocampus. *Nature.* 2002.415, p 1030-1034.) The infected cells can express GFP stably which makes it possible to follow neurons that have divided in vivo as they differentiate and migrate to sites within the brain. In addition, MuLV infection-GFP strategy permits a more precise comparison of the dividing speed between the THP treated cells and the non-treated cells by FACS analysis. Furthermore, this use of the retroviral infection strategy may also provide data for future application for future gene therapy purposes.

A strain of virus was used in which the GFP was inserted in frame with the authentic start codon of the internal ribosome entry site-transgene cassette which is positioned between the env gene and the 3' long terminal repeat. This virus vector exhibited replication kinetics similar to those of the wild-type MuLV and mediated efficient delivery of transgene (Logg, C. R. Tai, C. K. Logg, A. Anderson, W. F. Kasahara, N., A uniquely stable replication-competent retrovirus vector achieves efficient gene delivery in vitro and in solid tumors. Human Gene Therapy. 2001.8: p 921-932).

Neural progenitor and or stem cells (NP/SC) are prepared for ex-vivo expansion, i.e., to be contacted with one or more neuro-enhancing agents described in the present invention. Methods of obtaining and maintaining NP/SC are known in the art (Eriksson, P. S., E. Perfilieva, et al. (1998). "Neurogenesis in the adult human hippocampus." *Nat. Med.* 4 (1313-7, Song, H. J. C. F. Stevens7 et al. (2002). "Neural stem cells from adult hippocampus develop essential properties of functional CNS neurons. [comment]." *Nature Neuroscience* 5 (5): 438-45; van Praag, H., A. F. Schinder, et al. (2002). "*Functional neurogenesis in the adult hippocampus.*" Nature 415 (6875): 1030-4; Erlandsson, A., M. Enarsson, et al. (2001). "Immature neurons from CNS stem cells proliferate in response to platelet-derived growth factor" *Journal of Neuroscience* 21 (10): 3483-91). To this culture of cells, about 100 nm to about 1000 nm THP or another substantially equivalent variant neuro-enhancing molecule is added. Appropriate growth conditions are maintained to maximize mitosis of the NP/SC with minimal differentiation of the NP/SC, thus leading to a culture containing more NP/SC than present prior to the addition of one or more neuro-enhancing agents of the present invention. The expanded population of neural cells is then infused into an individual suffering from neuronal loss, or other neurological defect or damage, via intracerebroventricular infusion. The infusion of expanded cells is monitored to assess further proliferation, differentiation and survival.

Example 7

Neural Progenitor Proliferation in Dentate Granular Zone (DGZ) is Deficient in 3 Month Old Male 3×TgAD Mice Prior to Onset of Visible AD Pathology BrdU immunohistochemistry (IHC) was preformed on adjacent sections of IHC-labeled for Aβ. Sections were immunostained with BrdU antibody (Novus Biologicals) and imaged using 3I Marianas Imaging System with Zeiss Axiovert 200M interfaced with a Sony ICX-285 CCD CoolSnap HQ camera and Xenon 2-Gal Fast Excitation Source equipped with SlideBook unbiased quantitative stereology software. Results of un-biased quantitative stereological analyses indicate that at 3 months prior to the appearance of markers of Alzheimer's (AD) pathology, the BrdU-positive cell number was significantly lower in the 3×TgAD mouse dentate relative to non-Tg mouse dentate. This finding indicates basal neurogenesis in 3×TgAD mice DGZ is reduced prior to development of overt AD pathology. These results also suggest that the early neurogenic deficits, which were evident prior to visible Aβ and ptau, may contribute to etiology of AD.

Example 8

3α-hydroxy-5α-pregnan-20-one (THP) reverses the neurogenic deficits in 3xTgAD mice hippocampal dentate gyms THP increased BrdU incorporation in both non-Tg and 3xTgAD mice. A more pronounced and significant increase was observed in 3xTgAD mice with the greatest increase, 55+18% greater vs. vehicle control group, which occurred at 10 mg/kg BW. Analysis of total number of cells generated indicated that APα restored proliferation to that of normal nontransgenic mice thereby reversing the neurogenic deficit.

Cortices from brain hemisection of mice treated with THP or vehicle were collected at time of sacrifice for measurement of THP by GC/MS. Plasma was also collected at time of sacrifice. Three-month-old male non-Tg and 3xTgAD mice were subcutaneously injected with THP (1, 10, and 20 mg/kg BW) or vehicle (0.1% ethanol in PBS, n=4 in each group). The mice were sacrificed 24 hours later. THP concentration in plasma and brain were measured by GC/MS. THP was detectable in plasma and cortex in a linear dose dependent manner. An interesting finding is that 3xTgAD mice exhibited a consistently lower level of THP in both plasma and cortex relative to nontransgenic THP treated mice. In the 3xTgAD mouse cortex, a 10 mg/kg dose of THP results in a cortical level of 20 ng/g protein 24 hrs post injection.

Example 9

3α-hydroxy-5α-pregnan-20-one (THP) increased expression of proliferating cell nuclear antigen (PCNA) and cyclin dependent kinase 1 (CDK1/cdc2) in the hippocampus of 3xTgAD and non-Tg mice We sought to identify a medium throughput marker of proliferation that would allow us to detect proliferative efficacy in hippocampus with greater speed relative to unbiased stereological analyses. Thus, we conducted biochemical analyses in parallel to the stereological analyses to determine whether two well defined cell cycle related proteins, PCNA and CDK1/cdc2, would serve as biochemical indicators of proliferation in the hippocampus.

Brain samples derived from the same brains that underwent unbiased stereological analysis and GC/MC for THP detection were also analyzed by real-time RT-PCR and Western blot for expression of PCNA and CDK1 mRNA and protein. Results of these analyses indicate that APα induced a dose-dependent increase in PCNA mRNA in a pattern consistent with the stereological results in the 3xTgAD mice. Results of Western blot analyses indicate that 10 mg/kg APα induced greater PCNA and CDK1 protein expression in the hippocampi of 3xTgAD relative to the non-Tg mice which is consistent with the stereological data. Importantly, these data indicate that either mRNA or protein expression of PCNA can serve as an indicator of proliferation within the hippocampus to permit a first pass medium throughput analysis of the proliferative efficacy of APα across multiple doses and topical formulations.

Example 10

Phenotype of newly formed cells in 3α-hydroxy-5α-pregnan-20-one (THP) treated 3xTgAD mouse dentate gyrus are neuronal and astrocytic To verify the phenotype of the BrdU-positive cells in vivo, double or triple immunolabeling of BrdU-positive cells with neuronal markers Tuj1, MAP2, NeuN and astrocyte marker, GFAP, were performed in the 3xTgAD mouse hippocampi, which were treated with 10 mg/kg THP at 3 months and survived for 3-12 weeks. Under lower magnification, the majority of the BrdU-positive cells are observed in the SGZ or Hilus. The distribution of the newly formed cells is consistent with that observed by previous studies. Imaging showed co-localization of BrdU in NeuN positive cells, indicating that newly generated cells exhibit an early neuronal phenotype. Imaging also showed a newly formed granular cell layer integrated neuron with nuclear co-localization of BrdU and NeuN and a glial cell with BrdU positive nuclear and GFAP positive cytosol.

Neurons and glia are generated throughout adulthood from proliferating cells in two regions of the rat brain, the subventricular zone (SVZ) and the hippocampal SGZ. We stereologically analyzed the SVZ from 3xTgAD mice in the control and 10 mg/kg APα groups. Results of these analyses indicated that THP induced a 58% increase in BrdU-positive cells relative to the 3xTgAD untreated group. These data indicate THP increase BrdU incorporation in both SVZ and SGZ, but was more pronounced in SVZ.

Example 11

3α-hydroxy-5α-pregnan-20-one (THP) reversed the learning deficits of 3xTgAD mice To determine if there was a functional consequence of THP-induced neurogenesis, the impact of THP on both the learning and memory of a behavioral task shown to be dependent upon the generation of new neurons in the dentate gyrus, delayed trace conditioning was assessed. 3xTgAD and non-Tg background mice were prepared for behavioral testing and received a single s.c. injection of THP (10 mg/kg once) or vehicle 7 days prior to start of the learning trial. After injection, mice were housed for 7 days before the training process started. The rationale for the 7 day interim between exposure to THP and the start of the behavioral experiment was to allow time for the proliferation, migration and integration of newly generated neurons into the dentate gyms. Following the 7 day interim period, the behavioral testing commenced with a 5 day (35 trials/day) training learning phase to assess rate and magnitude learning performance. In each trial, mice were first exposed to a conditioned stimulation of a 85 dB tone for 250 ms; followed by a 250 ms delay, followed by the unconditioned 60 Hz shock for 100 ms. Introduction of the 250 ms delay between the conditioned and unconditioned stimuli requires the hippocampus to acquire the learned association between tone and shock.

Following the learning trial, mice were returned to their home cage, for another 7 day period and subsequently tested for memory of the learned association. The data indicate that at 3 months, 3xTgAD mice exhibit a learning deficit relative to the performance of normal non-Tg mice. In the normal high functioning non-Tg mice, with a concomitant high level of neurogenesis, THP did not augment the learning performance. In contrast, THP significantly increased the learning performance of 3xTgAD mice to a level comparable to non-Tg mice such that the performance of APα treated 3xTgAD mice was not statistically different from the normal non-Tg mouse.

AP α Reversed the Memory Deficits of 3xTgAD Mice

One week following the learning trial, mice were tested for memory of the learned association. Non-Tg mice exhibited slightly less than 50% of the conditioned response compared to a 28% response rate of 3xTgAD mice. THP did not significantly augment the memory performance of non-Tg mice. However, THP treated 3×TgAD mice exhibited a significant increase in memory to a level comparable to the normal non-Tg mice. Multivariant ANOVA analysis indicated significant differences for learning and memory in genotype (p=0.004) and days of training (0.04). No interaction occurred between days of training and genotype (p=0.997). Results of the behavioral analyses indicate that AP α enhanced the rate of learning in 3×TgAD mice, increased magnitude of the learning performance and reversed the memory deficit of 3×TgAD mice.

Example 12

3α-hydroxy-5α-pregnan-20-one (THP) significantly increased survival of BrdU labeled cells We sought to determine whether cell survival was directly attributable to THP exposure or whether cell survival was dependent on the training experience. Thus, the relationship between survival of BrdU positive cells and cognitive performance on the memory phase of the behavioral testing was analyzed. It was first determined whether the conditioning paradigm contributed to an increase in BrdU positive cells as this has been observed in behavioral paradigms in which the learning trials were 6-7 times greater than our 35/trials/day; eg >200+ trials/day. To determine the effect of training/learning, 3×TgAD mice were trained for 35 trials/day for 5 days and subsequently sacrificed at the end of the learning phase and brains processed for BrdU analysis by unbiased stereological analysis. The data demonstrate that the training/learning paradigm used in our behavioral analyses did not induce an increase in BrdU positive cells. In contrast, THP treated 3×TgAD mice exhibited a near doubling in the number of surviving cells generated 20 days prior to sacrifice. These data indicate that the mechanism of THP action is independent of training condition and is specific to THP.

THP Enhancement of Memory Function is Highly Correlated to the Number of Newly Formed BrdU Positive Cell Numbers We sought to determine the relationship between survival of BrdU positive cells and cognitive performance on the memory phase of the behavioral testing. Correlational analysis indicated a highly significant correlation between the number of surviving BrdU positive cells and memory performance for both the vehicle treated 3×TgAD mice and the APα treated 3×TgAD mice (Table 1).

TABLE 1

Correlation of survived BrdU cells with conditioned response (CR)

| | BrdU cells | % CR | CR/BrdU | R value |
|---|---|---|---|---|
| Vehicle (n = 10) | 652.8 | 28.33 | 0.0434 | 0.58 |
| APα (n = 12) | 1088 | 53.96 | 0.0496 | 0.68 |

Example 13

3α-hydroxy-5α-pregnan-20-one (THP) reduces immunocytochemically detectable β-amyloid and ptau expression in the 6 month old 3×TgAD male mouse CA1 region of the hippocampus Triple transgenic mice were sacrificed at different ages as indicated, brain sections immunostained with anti-Amyloid $\beta_1 42$ antibody and observed with peroxidase-DAB. Results of our assessment of pathology development replicate those of the LaFerla group and indicate that results from our laboratory are consistent with previously published characterization. At 3 months, cellular Aβ immunoreactivity (IR) was barely visible. At 6, 9 and 12 months, intracellular Aβ IR was apparent and intensity increased with age. Extraneuronal Aβ IR was rarely observed in 9-month-old 3×TgAD hippocampi but was consistently present in the hippocampus of 12-month-old 3×TgAD mice. Preliminary results indicate an age-dependent increase of Aβ levels in the cortex which is also in agreement with published reports.

In a pilot project to determine the impact of longterm exposure to APα, the impact of THP, 10 mg/kg s.c. thrice weekly for 3 months, on the progression of Alzheimer's disease (AD) pathology in 3-6 month old 3×TgAD mice was investigated. Mouse brain hemisphere sections were immunostained with specific antibody (6E10) against Aβ or HT7, which recognizes tau and PHF-tau between residue 159 and 163 and visualized with FITC conjugated second antibody. Observation of immunoreactivity indicated that both Aβ and ptau IR were primarily localized within neuronal cell bodies. Quantitative analysis using SlideBook supported color mask and automatic color-cell counting system (3i Intelligent Imaging System) indicated that APα reduced the level of AD pathology markers in 3×TgAD mouse hippocampal CA1. Results of this pilot project indicate that THP reduced AD pathology burden in the subicular region of the hippocampus.

Figure 11:
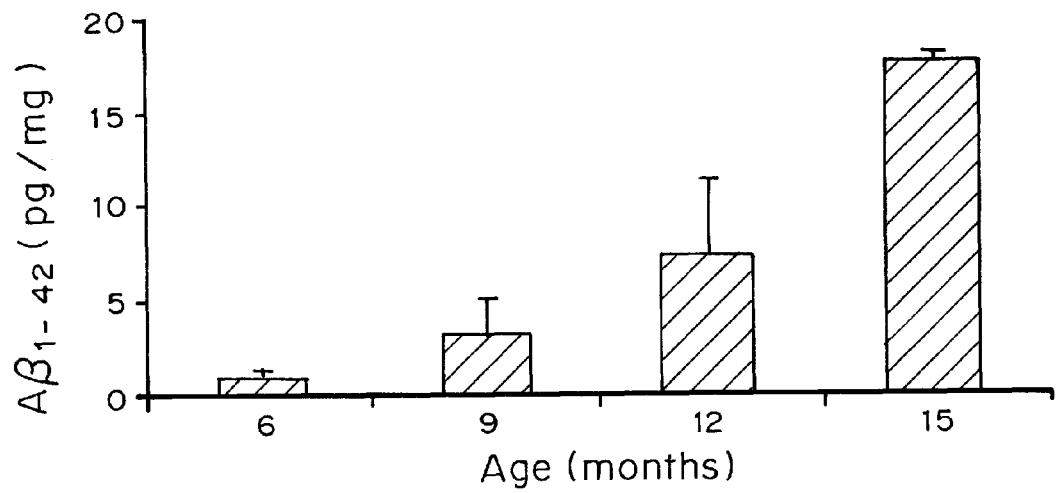
FIG. 11 is a graph showing the concentration of $A\beta_{1-42}$ (pg/mg) as a function of age of male mice (months) transgenic for Alzheimer's disease

In another experiment, THP (10 mg/kg/week, administered once a week for 6 months) was administered to 9- and 12-month male mice transgenic for Alzheimer's disease (3×Tg-AD). The 9 month old animals were started on THP at 3 months of age prior to the development of beta amyloid, whereas the 12 month old animals were begun at 6 months of age when beta amyloid had already begun to accumulate within neurons. Typically, the development of intraneuronal beta amyloid is seen in 6 and 9 month old animals and the development of plaques in 12 month old animals. Plaques are rarely seen in 9 month old animals. This is shown in FIG. 11.

Figure 12:
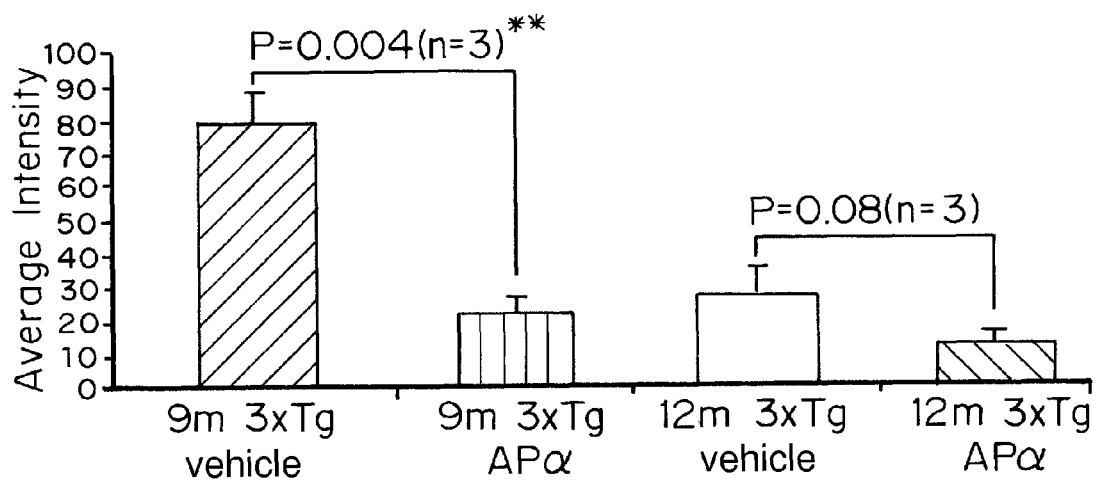
FIG. 12 is a graph showing the effect of THP on β-amyloid 6E10 (56 KD) (average intensity) expression in the cerebral cortex of 9- and 12-month male mice transgenic for Alzheimer's disease.

The results of THP administration are shown in FIG. 12. The graph shows that THP significantly decreased the amount of beta amyloid in the cerebral cortex of male mice transgenic for Alzheimer's disease. Western Blot analysis showed a form of beta amyloid termed Abeta*56, which is the oligomer (multiple amyloid beta peptides joined together) that, in animal studies, leads to memory loss in both transgenic Alzheimer mouse models and in rats injected with Abeta*56 (Lesne et al., Nature, 440, 352-357 (Mar. 16, 2006)). Thus, reducing Abeta*56 has the potential for preventing or reversing memory loss. In the 12 month old animals, the level of Abeta*56 was much lower, likely due to the development of beta amyloid plaques in these animals, which reduces the amount of Abeta*56.

Figure 13A:
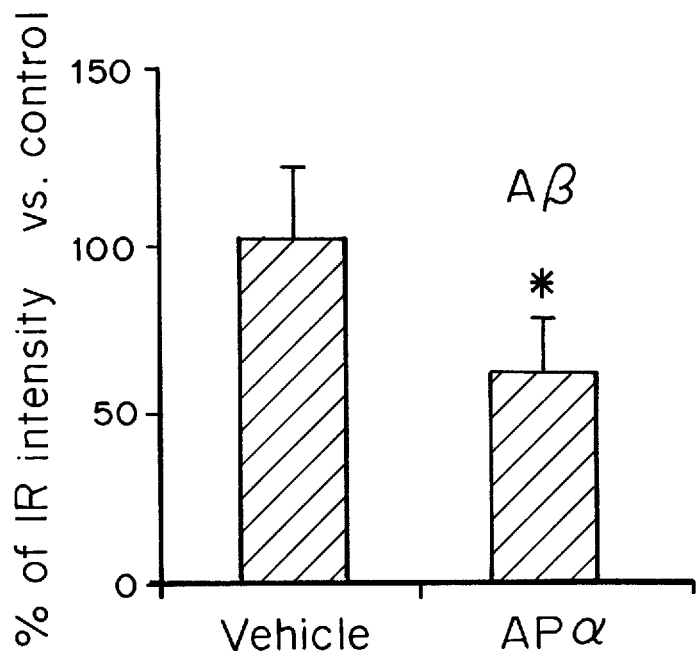
FIGS. 13a and 13b are graphs showing the effect of THP on the concentration of Abeta*56 (% of infrared intensity) and phosphorylated tau*% of infrared intensity), respectively.
Figure 13B:
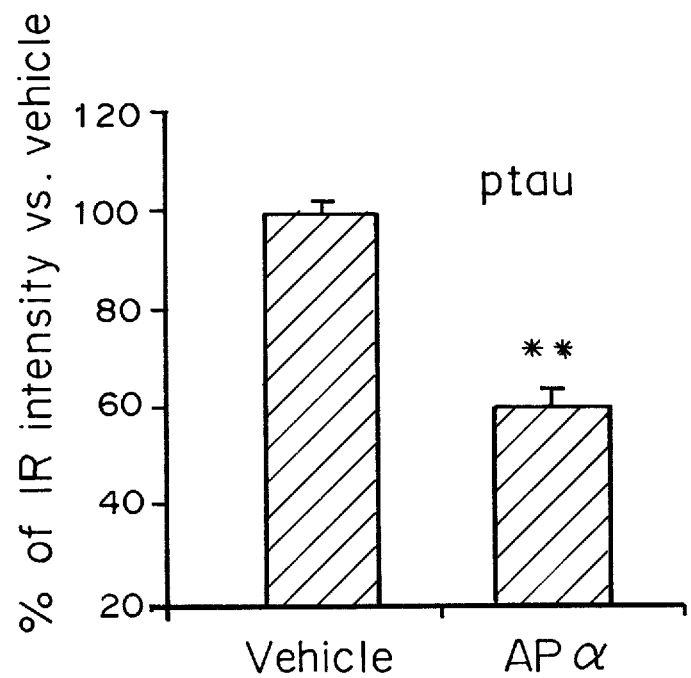

Immunocytochemical detection of beta amyloid showed that administration of THP substantially decreases Abeta*56 in hippocampal neurons. THP also decreases the immunoreactivity of phosphorylated tau, which is the basis for neurofibrillary tangles. The quantitation of the immunofluorescent signals for Abeta*56 and phosphorylated tau is shown in FIG. 13.

Example 14

Dose-response and time course of 3α-hydroxy-5α-pregnan-20-one (THP)-induced proliferation in human neural progenitor cells (hNPC)

To determine the impact of THP on hNPC cell proliferation, a dose response (pM-nM) experiment was first performed. Results of these analyses indicate:

a. THP, at doses within an achievable therapeutic range, increased human neural progenitor cell proliferation by 50%. Results of dose response analyses indicate that THP promoted human neural stem cell proliferation in a biphasic dose dependent fashion.

b. THP-induced human neural stem cell proliferation was first evident at 1 nM and maximal at 100 nM. Maximal proliferative efficacy was asymptotic at 100 nM, sustained at 250 and 500 nM and diminished at 1000 nM.

c. THP-induced hNPC proliferation was linear and evident at 3 hours and reached maximum at 6 hours.

d. Efficacy of THP as a neurogenic factor exceeded that of bFGF+heparin in promoting human neural progenitor cell proliferation.

e. Findings derived from hNPCs replicate results of APα-induced proliferation of rodent hippocampal NPCs.

Example 15

3α-hydroxy-5α-pregnan-20-one (THP) increases hNPC proliferation while not changing neuronal phenotype To determine the impact of THP on the stability of hNPC phenotype, hNPCs were double labeled with BrdU, Tuj1 and MAP2, or GFAP. Quantitative analysis of phenotype (DAPI-positive blue nuclei as marker of total cell number) indicated that APα significantly increased the number of BrdU positive hNPCs while not changing the proportion of Tuj1, MAP2 or GFAP cells vs. vehicle treated hNPCs.

AP α-Induced hNPC Cell Proliferation is Blocked by GABAAR Antagonist

Previously, we demonstrated that APα-induced rat NPC proliferation is mediated by GABAAR, as the GABAAR antagonist bicuculline abolished the APα-induced intracellular calcium concentration increase, required for APα-induced rNPC cell proliferation. To determine whether the same mechanisms of APα-induced proliferation in rodent derived NPCs could be generalized to humans, we determined the requirement of the GABAAR by antagonizing the GABAAR with bicucculline followed by assessment of APα-induced hNPC cell proliferation. Results of those analyses indicate that 250 nM APα was as efficacious a proliferative factor as the positive control, bFGF. Both vehicles, alcohol and DMSO, had no significant effect on basal hNPC proliferation. Bicuculline completely antagonized, APα-induced hNPC proliferation. These results indicate that as in rNPCs, APα-induced proliferation requires the GABAAR.

Human Neural Progenitor Cells (hNPC) Express a Specific Combination of GABAAR (GBRC) Subunits.

Activation of GABAAR in mature neurons leads to hyperpolarization via an influx of chloride. In contrast, in immature neurons and neural progenitors activation of the GABAAR leads to a depolarization through an efflux of chloride. It is hypothesized that hNPCs responsive to APα will exhibit a GABAAR phenotype that is comparable to extrasynaptic GABAAR. The tonic conductances of the extrasynaptic GABAARs may be more conducive to depolarization required for opening voltage dependent L-type calcium channels and downstream signaling cascades required for cell cycle activation.

To determine GABAAR receptor subunit expression in hNPC cells, reverse transcriptase PCR (RT-PCR) using total RNA extracted from cultured hNPC and human fetal brain was performed, the latter used as a control to verify all the primers used are functional in RT-PCR. cDNA from total human fetal brain total RNA showed positive amplification of GBRC subunits. In contrast, α2 and α5, but not α1 and α4 were expressed in hNPC. In addition, a much higher expression of δ subunit in hNPC was also observed. These results are consistent with recent data in the literature showing that the APα binding pocket required for direct activation of the GBRC requires a pocket formed by the interface between α and β subunits in which APα spans the interface between the 2 subunits.

All patents cited in this specification are herein incorporated by reference as if each individual patent were specifically and individually indicated to be incorporated by reference.

Although the foregoing embodiments of the invention has been described in some detail by way of illustration and example for purposes of clarity and understanding, it will be readily apparent to those of ordinary skill in the art in light of the teachings of this invention that certain changes and modifications may be made thereto without departing from the scope of the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for reversing learning or memory deficits in a human patient who has lost some amount of neurological function as a result of a neurological disease, a neurological injury, or age-related neurological decline or impairment, the method comprising administering to the human patient a composition comprising an effective amount of 3-hydroxy-5-pregnan-20-one to provide neuroprotection, reduce declines in learning or memory, or combinations thereof,
wherein the 3-hydroxy-5-pregan-20-one is administered once a week or less frequently.

2. The method of claim 1 for reversing memory deficits in a human patient who has lost some amount of neurological function as a result of a neurological disease, a neurological injury, or age-related neurological decline or impairment, the method comprising administering to the human patient a composition comprising an effective amount of 3-hydroxy-5-pregan-20-one
wherein the 3-hydroxy-5-pregan-20-one is administered at a dosage of between 0.17 mg/kg and 8.33 mg/kg.

3. The method according to claim 1, wherein the 3α-hydroxy-5-pregnan-20-one is administered once a week.

4. The method of claim 2, wherein the 3-hydroxy-5-pregan-20-one is administered for a period of about one month or longer.

5. The method of claim 4, wherein the 3-hydroxy-5-pregan-20-one is administered for a period of about six months or longer.

6. The method of claim 5, wherein the 3-hydroxy-5-pregan-20-one is administered for a period of about one year or longer.

7. The method of claim 2, wherein the 3α-hydroxy-5-pregnan-20-one is administered at a dosage of between 0.83 mg/kg and 8.33 mg/kg.

8. The method of claim 2, wherein the learning deficit is the result of a neurological disease.

9. The method of claim 2, wherein the composition is administered via injection, infusion, implantation, inhalation, orally or topically.

10. The method of claim 1, wherein the deficits are learning deficits.

11. The method of claim 10, wherein the 3α-hydroxy-5-pregnan-20-one is administered at a dosage of between 50 and 500 mg.

12. The method of claim 10, wherein the 3-hydroxy-5-pregnan-20-one is administered for a period of about one month or longer.

13. The method of claim 12, wherein the 3-hydroxy-5-pregnan-20-one is administered for a period of about six months or longer.

14. The method of claim 12, wherein the 3-hydroxy-5-pregnan-20-one is administered for a period of about one year or longer.

15. The method of claim 10, wherein the 3α-hydroxy-5-pregnan-20-one is administered at a dosage of between 0.83 mg/kg and 8.33 mg/kg.

16. The method of claim 10, wherein the learning deficit is the result of a neurological disease.

17. The method of claim 10, wherein the composition is administered via injection, infusion, implantation, inhalation, orally or topically.

18. The method of claim 2, wherein the 3α-hydroxy-5-pregnan-20-one is administered at a dosage of between 50 and 500 mg.

19. The method of claim 16, wherein the neurological disease is Alzheimer's disease.

20. The method of claim 19, wherein the 3α-hydroxy-5-pregnan-20-one is in an effective amount to reduce β-amyloid accumulation in the brain.

21. The method of claim 8, wherein the neurological disease is Alzheimer's disease.

22. The method of claim 21, wherein the 3α-hydroxy-5-pregnan-20-one is in an effective amount to reduce β-amyloid accumulation in the brain.

* * * * *

UNITED STATES PATENT AND TRADEMARK OFFICE
CERTIFICATE OF CORRECTION

PATENT NO. : 8,969,329 B2
APPLICATION NO. : 12/526604
DATED : March 3, 2015
INVENTOR(S) : Roberta Diaz Brinton and Jun Ming Wang Page 1 of 1

It is certified that error appears in the above-identified patent and that said Letters Patent is hereby corrected as shown below:

In the Specification

Column 1, Line 22, before "BACKGROUND OF THE INVENTION", insert the following paragraph:
-- STATEMENT REGARDING FEDERALLY SPONSORED RESEARCH OR DEVELOPMENT
This invention was made with government support under U01 AG047222, U01 AG031115, and AG046148 awarded by the National Institutes of Health. The government has certain rights in the invention. --

Signed and Sealed this
Twenty-fifth Day of March, 2025

Coke Morgan Stewart
*Acting Director of the United States Patent and Trademark Office*